United States Patent
Teles et al.

(10) Patent No.: US 10,316,007 B2
(45) Date of Patent: *Jun. 11, 2019

(54) PART-STREAM DISTILLATION

(71) Applicants: BASF SE, Ludwigshafen (DE); Dow Global Technologies LLC, Midland, MI (US)

(72) Inventors: Joaquim Henrique Teles, Waldsee (DE); Dominic Riedel, Lampertheim (DE); Bianca Seelig, Milan (IT); Philip Kampe, Bensheim (DE); Markus Weber, Limburgerhof (DE); Alexander Schroeder, Wattenheim (DE); Andrei-Nicolae Parvulescu, Ruppertsberg (DE); Ulrich Mueller, Neustadt (DE); Daniel Urbanczyk, Griesheim (DE); Meinolf Weidenbach, Stade (DE); Werner J. Witzl, Stade (DE); Holger Baer, Stade (DE)

(73) Assignees: BASF SE, Ludwigshafen (DE); DOW GLOBAL TECHNOLOGIES LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/521,924

(22) PCT Filed: Oct. 27, 2015

(86) PCT No.: PCT/EP2015/074839
§ 371 (c)(1),
(2) Date: Apr. 26, 2017

(87) PCT Pub. No.: WO2016/066629
PCT Pub. Date: May 6, 2016

(65) Prior Publication Data
US 2018/0230117 A1    Aug. 16, 2018

(30) Foreign Application Priority Data

Oct. 27, 2014    (EP) .................................. 14190535

(51) Int. Cl.
*C07D 301/12*    (2006.01)
*B01D 3/14*    (2006.01)
(Continued)

(52) U.S. Cl.
CPC ........... *C07D 301/12* (2013.01); *B01D 3/146* (2013.01); *C07D 301/32* (2013.01); *C07D 303/04* (2013.01)

(58) Field of Classification Search
CPC .................................................... C07D 301/12
(Continued)

(56) References Cited

U.S. PATENT DOCUMENTS

| 5,194,675 | A  |   | 3/1993 | Joerg et al. |
| 9,732,054 | B2 | * | 8/2017 | Teles .................... C07D 301/12 |

(Continued)

FOREIGN PATENT DOCUMENTS

| EP | 0 427 062 A2 | 5/1991 |
| EP | 1 606 273 A1 | 12/2005 |

(Continued)

OTHER PUBLICATIONS

U.S. Pat. No. 8,957,244, Feb. 17, 2015, 2014/0148614 A1, Schneider et al.

(Continued)

*Primary Examiner* — Taylor V Oh
(74) *Attorney, Agent, or Firm* — Oblon, McClelland, Maier & Neustadt, L.L.P.

(57) ABSTRACT

A continuous process for preparing propylene oxide proceeds by (a) reacting propene with hydrogen peroxide in a reaction apparatus in the presence acetonitrile as solvent, (Continued)

obtaining a stream S0 containing propylene oxide, acetonitrile, water, at least one further component B; (b) separating propylene oxide from S0, obtaining stream S1 containing acetonitrile, water and B; (c) dividing S1 into streams S2 and S3; (d) subjects S3 to vapor-liquid fractionation in a first fractionation unit, obtaining vapor fraction stream S4a being depleted, relative to S3, of at least one of B and obtaining liquid bottoms stream S4b, and subjecting at least part of vapor fraction stream S4a to vapor-liquid fractionation in a second fractionation unit, obtaining vapor fraction stream S4c and liquid bottoms stream S4 being depleted, relative to S4a, of at least one of B; (e) recycling at least a portion of S4 to (a).

22 Claims, 2 Drawing Sheets

(51) Int. Cl.
  *C07D 301/32* (2006.01)
  *C07D 303/04* (2006.01)
(58) Field of Classification Search
  USPC .......................................................... 549/531
  See application file for complete search history.

(56) References Cited

U.S. PATENT DOCUMENTS

| | | |
|---|---|---|
| 2004/0068128 A1 | 4/2004 | Teles et al. |
| 2006/0113180 A1 | 6/2006 | Patrascu et al. |
| 2007/0043226 A1 | 2/2007 | Muller et al. |
| 2011/0065939 A1 | 3/2011 | Teles et al. |

FOREIGN PATENT DOCUMENTS

| | | |
|---|---|---|
| WO | WO 2007/000396 A1 | 1/2007 |
| WO | WO 2011/006990 A1 | 1/2011 |

OTHER PUBLICATIONS

U.S. Appl. No. 14/787,956, filed Apr. 28, 2016, 2016/0115140 A1, Teles et al.
U.S. Appl. No. 15/246,028, filed Dec. 15, 2016, 2016/0362387 A1, Teles et al.
U.S. Pat. No. 9,428,438, Aug. 30, 2016, 2014/0148617 A1, Fries et al.
U.S. Appl. No. 14/907,714, filed Nov. 17, 2016, 2016/0332152 A1, Parvulescu et al.
U.S. Appl. No. 15/030,754, filed Sep. 1, 2016, 2016/0250624 A1, Parvulescu et al.
U.S. Appl. No. 14/760,621, filed Dec. 10, 2015, 2015/0353808 A1, Kimura et al.
U.S. Appl. No. 14/090,231, filed Jun. 5, 2014, 2014/0150485 A1, Weickert et al.
U.S. Appl. No. 14/907,998, filed Jun. 23, 2016, 2016/0176834 A1, Teles et al.
U.S. Appl. No. 14/765,471, filed Jan. 7, 2016, 2016/0002058 A1, Parvulescu et al.
U.S. Pat. No. 9,688,648, Jun. 27, 2017, 2016/0185741 A1, Teles et al.
U.S. Appl. No. 14/764,354, filed Dec. 24, 2015, 2015/0368115 A1, Parvulescu et al.
U.S. Pat. No. 9,636,668, May 2, 2017, 2014/0135556 A1, Gaab et al.
U.S. Appl. No. 14/169,895, filed Jul. 31, 2014, 2014/0213832 A1, Gaab et al.
U.S. Appl. No. 14/504,419, filed Jan. 22, 2015, 2015/0025250 A1, Ayesa et al.
U.S. Pat. No. 9,518,211, Dec. 13, 2016, 2015/0361325 A1, Kimura et al.
U.S. Pat. No. 9,598,326, Mar. 21, 2017, 2014/0142361 A1, Gaab et al.
U.S. Appl. No. 14/902,231, filed Dec. 22, 2016, 2016/0368887 A1, Dehn et al.
U.S. Pat. No. 9,370,771, Jun. 21, 2016, 2014/0208650 A1, Gaab et al.
U.S. Appl. No. 14/783,531, filed Mar. 3, 2016, 2016/0060434 A1, Reinicker et al.
U.S. Pat. No. 8,987,497, Mar. 24, 2015, 2014/0128622 A1, Vautravers et al.
U.S. Pat. No. 9,371,239, Jun. 21, 2016, 2014/0163243 A1, Parvulescu et al.
U.S. Appl. No. 14/896,097, filed May 12, 2016, 2016/0130160 A1, Baer et al.
U.S. Appl. No. 14/150,239, filed Jul. 17, 2014, 2014/0200379 A1, Josch et al.
U.S. Appl. No. 14/897,379, filed May 26, 2016, 2016/0145171 A1, Spannhoff et al.
U.S. Appl. No. 14/894,432, filed May 5, 2016, 2016/0122296 A1, Parvulescu et al.
U.S. Appl. No. 14/902,247, filed Dec. 22, 2016, 2016/0368843 A1, Teles et al.
U.S. Appl. No. 14/892,635, filed Apr. 21, 2016, 2016/0109067 A1, Kimura et al.
U.S. Appl. No. 14/759,522, filed Dec. 10, 2015, 2015/0353446 A1, Feyen et al.
U.S. Pat. No. 9,561,995, Feb. 7, 2017, 2016/0221920 A1, Maurer et al.
U.S. Appl. No. 14/906,471, filed Jun. 16, 2016, 2016/0172708 A1, Porta Garcia et al.
U.S. Appl. No. 14/911,747, filed Jun. 30, 2016, 2016/0186932 A1, Weickert et al.
U.S. Appl. No. 14/911,756, filed Jul. 14, 2016, 2016/0201853 A1, Weickert et al.
U.S. Appl. No. 15/314,560, filed Nov. 29, 2016, Riedel et al.
U.S. Appl. No. 14/908,042, filed Jun. 23, 2016, 2016/0176835 A1, Riedel et al.
U.S. Appl. No. 15/106,048, filed Oct. 27, 2016, 2016/0312149 A1, Vautravers et al.
U.S. Pat. No. 9,464,029, Oct. 11, 2016, 2015/0376111 A1, Boehling et al.
U.S. Appl. No. 14/911,789, filed Jul. 14, 2016, 2016/0201854 A1, Weickert et al.
U.S. Appl. No. 15/102,586, filed Nov. 3, 2016, 2016/0318860 A1, Vautravers et al.
U.S. Appl. No. 15/034,249, filed Sep. 15, 2016, 2016/0264543 A1, Vautravers et al.
U.S. Appl. No. 14/909,785, filed Jun. 30, 2016, 2016/0185762 A1, Teles et al.
U.S. Appl. No. 15/509,228, filed Mar. 7, 2017, Riedel et al.
U.S. Pat. No. 9,640,839, May 2, 2017, 2016/0172709 A1, Porta Garcia et al.
U.S. Appl. No. 15/109,601, filed Nov. 10, 2016, 2016/0325228 A1, Feyen et al.
U.S. Appl. No. 15/033,824, filed Sep. 29, 2016, 2016/0279621 A1, Parvulescu et al.
U.S. Appl. No. 15/308,755, filed Nov. 3, 2016, Vautravers et al.
U.S. Appl. No. 15/312,033, filed Apr. 20, 2017, 2017/0107168 A1, Vautravers et al.
U.S. Appl. No. 15/509,527, filed Mar. 8, 2017, Parvulescu et al.
U.S. Appl. No. 14/497,718, filed Apr. 2, 2015, 2015/0090610 A1, Dolan et al.
U.S. Appl. No. 14/498,342, filed Apr. 2, 2015, 2015/0094202 A1, Dolan et al.
U.S. Appl. No. 14/498,363, filed Apr. 2, 2015, 2015/0090226 A1, Dolan et al.
U.S. Appl. No. 14/498,388, filed Apr. 2, 2015, 2015/0090231 A1, Dolan et al.
U.S. Appl. No. 14/498,407, filed Apr. 2, 2015, 2015/0090611 A1, Dolan et al.

(56) References Cited

OTHER PUBLICATIONS

U.S. Appl. No. 14/498,435, filed Apr. 2, 2015, 2015/0090344 A1, Dolan et al.
U.S. Appl. No. 14/649,637, filed Oct. 22, 2015, 2015/0298983 A1, Maurer et al.
U.S. Appl. No. 15/305,556, filed Feb. 16, 2017, 2017/0044421 A1, Parvulescu et al.
U.S. Appl. No. 15/305,549, filed Feb. 9, 2017, 2017/0037296 A1, Kimura et al.
U.S. Appl. No. 15/033,402, filed Sep. 8, 2016, 2016/0256859 A1, Parvulescu et al.
U.S. Appl. No. 15/315,143, filed Nov. 30, 2016, Riedel et al.
U.S. Pat. No. 9,446,390, Sep. 20, 2016, 2015/0343431 A1, Parvulescu et al.
U.S. Appl. No. 15/316,220, filed Dec. 5, 2016, Maurer et al.
U.S. Appl. No. 15/121,061, filed Dec. 22, 2016, 2016/0367468 A1, Graham et al.
U.S. Pat. No. 9,540,305, Jan. 10, 2017, 2015/0344394 A1, Parvulescu et al.
U.S. Appl. No. 15/518,945, filed Apr. 13, 2017, Maurer et al.
U.S. Appl. No. 15/518,791, filed Apr. 13, 2017, Pelzer et al.
U.S. Appl. No. 15/508,725, filed Mar. 3, 2017, Edgington et al.
U.S. Appl. No. 15/521,924, filed Apr. 26, 2017, Teles et al.
International Search Report and Written Opinion dated Jan. 28, 2016 in PCT/EP2015/074839.
International Preliminary Report on Patentability and Written Opinion dated May 2, 2017 in PCT/EP2015/074839.
K. J. Lissant, et al., "Making and Breaking Emulsions", Res. Lab., Petrolite Corp., St. Louis, Missouri, Emulsion Technology, Chapter 2, 1974, 57 pages.
S. E. Taylor, "Resolving Crude Oil Emulsions", Chemistry & Industry, Oct. 19, 1992, pp. 770-773.

\* cited by examiner

PART-STREAM DISTILLATION

The present invention relates to a continuous process for the preparation of propylene oxide wherein in a downstream acetonitrile solvent recovery stage, a stream S1 containing the solvent acetonitrile and at least one component which has a normal boiling point which is higher than the normal boiling point of acetonitrile, wherein the decadic logarithm of the octanol-water partition coefficient (log $K_{OW}$) of the at least one component B, measured at 25° C., is greater than zero, is divided into two streams S2 and S3, wherein the total weight of S3 relative to the total weight of S1 is in the range of from 0.01 to 25%. The stream S3 is subjected to a vapor-liquid fractionation comprising to serially coupled fractionation units, and a stream S4, obtained from the vapor-liquid fractionation and depleted of the at least one component B, optionally after further work-up, is recycled as solvent stream to the epoxidation reaction.

Especially in industrial-scale continuous processes for the epoxidation of propene in acetonitrile as solvent, one of the key features of the overall process is the recycling of the solvent back into the epoxidation step. An advantageous process which allows to effectively recycle acetonitrile is described in WO 2011/006990 A1. This document discloses a method for the separation of the acetonitrile from water, which method can be advantageously included in a continuous process for the preparation of propylene oxide in acetonitrile as solvent. Carrying out this epoxidation process, it was found that although the process allows to achieve excellent results, in particular with regard to the recycling of acetonitrile, certain impurities, contained in in at least one of the starting materials in the acetonitrile or in the hydrogen peroxide employed for the epoxidation reaction or obtained during the epoxidation reaction as by-products or side-products or formed during at least one of the work-up stages which are preferably carried out downstream the epoxidation reaction, may tend to a accumulate in the acetonitrile recycling stream. These impurities may further tend to have a negative influence on the performance of the heterogeneous catalyst which is preferably employed in the epoxidation process, in particular a zeolite-based catalyst having framework structure MWW and containing Ti. Such a decrease in performance may be observed either in a decrease in selectivity and/or in activity of the catalyst.

Therefore, it was an object of the present invention to provide an economically advantageous continuous process for the preparation of propylene oxide in acetonitrile as solvent which allows to essentially avoid the accumulation of such impurities in the recycling acetonitrile solvent stream.

Usually, if such impurities accumulate in a certain stream, the stream is subjected to one or more suitable separation stages such as distillation stages which, if carried out under suitable distillation conditions, may result in a stream depleted of the impurities. However, in particular in industrial-scale processes, subjecting a solvent recycling stream to such separation stages necessarily involves considerable investment and energy consumption, due to the usually high flow rates and the thus resulting large apparatuses.

Surprisingly, however, it was found that for the separation of impurities from an acetonitrile recycling stream in a continuous process for the preparation of propylene oxide, these disadvantage can be avoided by subjecting only a fraction of a specific recycling stream to impurity separation using a specifically designed fractionation unit, and leaving the major portion of this specific recycling stream untreated. For the impurities which were found to be critical, it was surprisingly found that the performance of the catalyst can be ensured over a very long period of time although only said minor fraction of a recycling stream is subjected to impurity separation.

Therefore, the present invention relates to a continuous process for the preparation of propylene oxide, comprising
(a) reacting propene, optionally admixed with propane, with hydrogen peroxide in a reaction apparatus in the presence of acetonitrile as solvent, obtaining a stream S0 leaving the reaction apparatus, S0 containing propylene oxide, acetonitrile, water, at least one further component B, optionally propene and optionally propane, wherein the normal boiling point of the at least one component B is higher than the normal boiling point of acetonitrile and wherein the decadic logarithm of the octanol-water partition coefficient (log $K_{OW}$) of the at least one component B is greater than zero;
(b) separating propylene oxide from S0, optionally after having separated propene and optionally propane, obtaining a stream S1 containing acetonitrile, water and the at least one further component B;
(c) dividing S1 into two streams S2 and S3, wherein the total weight of S3 relative to the total weight of S1 is in the range of from 0.01 to 25%;
(d) subjecting S3 to a vapor-liquid fractionation in a first fractionation unit, obtaining a vapor fraction stream S4a being depleted, relative to S3, of at least one of the at least one component B and obtaining a liquid bottoms stream S4b, and subjecting at least part of the vapor fraction stream S4a to a vapor-liquid fractionation in a second fractionation unit, obtaining a vapor fraction stream S4c and a liquid bottoms stream S4 being depleted, relative to S4a, of at least one of the at least one component B;
(e) recycling at least a portion of S4, optionally after work-up, to (a), and recycling at least a portion of S2, optionally after work-up, to (a).

Step (a)

According to step (a) of the present invention, propene, optionally admixed with propane, is reacted with hydrogen peroxide in a reaction apparatus in the presence of acetonitrile as solvent.

Generally, there are no specific restrictions how propene, optionally admixed with propane, is reacted with hydrogen peroxide, provided that the stream S0 is obtained leaving the reaction apparatus, which stream S0 contains propylene oxide, acetonitrile, water, the at least one further component B, and optionally propene and optionally propane.

Generally, it is conceivable to use a pure or essentially pure propene as starting material and as stream subjected to the epoxidation in (a). Preferably, a mixture of propene and propene is used. If a mixture of propene and propane is used as stream subjected to the epoxidation in (a), the weight ratio of propene:propane is preferably at least 7:3. For example, commercially available propene can be employed which may be either a polymer grade propene or a chemical grade propene. Typically, polymer grade propene has a propene content in the range of from 99 to 99.8 weight-% and a propane content in the range of from 0.2 to 1 weight-%. Chemical grade propene typically has a propene content in the range of from 92 to 98 weight-% and a propane content in the range of from 2 to 8 weight-%. According to a preferred embodiment of the present invention, a mixture of propene and propane is subjected to the epoxidation which has a propene content in the range of from 99 to 99.8 weight-% and a propane content in the range of from 0.2 to 1 weight-%. Therefore, the process of the present invention preferably comprises (a) reacting propene, admixed with propane, with hydrogen peroxide in a reaction apparatus in the presence of acetonitrile as solvent, obtaining a stream S0 leaving the reaction apparatus, S0 containing propylene oxide, acetonitrile, water, at least one further component B, propane and optionally propene, wherein the normal boiling point of the at least one component B is higher than the normal boiling point of acetonitrile and wherein the decadic logarithm of the octanol-water partition coefficient (log $K_{OW}$) of the at least one component B is greater than zero.

Preferably, the epoxidation reaction in (a) is carried out in the presence of at least one suitable catalyst, preferably in the presence of at least one suitable heterogeneous catalyst. Even more preferably, the at least one suitable catalyst comprises at least one zeolite which, in particular, contains Ti. Preferably, the at least one zeolite containing Ti has framework structure MWW. Even more preferably, this zeolite containing Ti and having framework structure MWW, referred to hereinunder as TiMWW, contains at least one further heteroatom besides Ti. Among such further heteroatoms, Zn is most preferred. Such a zeolite containing Zn and Ti and having framework structure MWW is referred to hereinunder as ZnTiMWW.

The catalysts, especially preferably the titanium zeolite catalysts and still more preferably TiMWW or ZnTiMWW, in particular ZnTiMWW, can be employed as powder, as granules, as microspheres, as shaped bodies having, for example, the shape of pellets, cylinders, wheels, stars, spheres and so forth, or as extrudates such as extrudates having, for example, a length of from 1 to 10, more preferably of from 1 to 7 and still more preferably of from 1 to 5 mm, and a diameter of from 0.1 to 5, more preferably of from 0.2 to 4 and especially preferably of from 0.5 to 2 mm.

The preparation of such preferred TiMWW catalysts is described, e.g., in US 2007043226 A1, in particular in Examples 3 and 5 of US 2007043226 A1.

As far as the preferred ZnTiMWW catalyst is concerned, it is still more preferred to employ this catalyst in the form of a micropowder or in the form of a molding, wherein the molding preferably contains said micropowder.

Said ZnTiMWW catalyst in the form of a micropowder is preferably characterized by the following features and embodiments, including the combinations of embodiments according to the given dependencies:

1. A micropowder, the particles of which having a Dv10 value of at least 2 micrometer, said micropowder comprising mesopores having an average pore diameter (4 V/A) in the range of from 2 to 50 nm as determined by Hg porosimetry according to DIN 66133, and comprising, based on the weight of the micropowder, at least 95 weight-% of a microporous aluminum-free zeolitic material of structure type MWW containing titanium and zinc (ZnTiMWW). The Dv10 value is understood as being determined according to Reference Example 2 of the present invention.
2. The micropowder of embodiment 1, having a Dv10 value in the range of from 2 to 5.5 micrometer, preferably from 3 to 5.5 micrometer.
3. The micropowder of embodiment 1 or 2, having a Dv50 value in the range of from 7 to 25 micrometer and a Dv90 value in the range of from 26 to 85 micrometer. The Dv50 and Dv90 values are understood as being determined according to Reference Example 2 of the present invention.
4. The micropowder of any of embodiments 1 to 3, wherein the mesopores have an average pore diameter (4 V/A) in the range of from 10 to 50 nm, preferably of from 15 to 40 nm, more preferably of from 20 to 30 nm, as determined by Hg porosimetry according to DIN 66133.
5. The micropowder of any of embodiments 1 to 4, additionally comprising macropores having an average pore diameter (4 V/A) in the range of from more than 50 nm, said macropores preferably having an average pore diameter in the range of from 0.05 to 3 micrometer, as determined by Hg porosimetry according to DIN 66133.
6. The micropowder of any of embodiments 1 to 5, wherein the micropores of the ZnTiMWW have an average pore diameter in the range of from 1.10 to 1.16 nanometer as determined by nitrogen adsorption according to DIN 66135.
7. The micropowder of any of embodiments 1 to 6, comprising, based on the weight of the micropowder, at least 99 weight-%, preferably at least 99.7 weight-% of the ZnTiMWW.
8. The micropowder of any of embodiments 1 to 7, wherein the ZnTiMWW contains zinc in an amount of from 1.0 to 2.0 weight-%, preferably of from 1.2 to 1.9 weight-%, more preferably of from 1.4 to 1.8 weight-%, calculated as Zn and based on the weight of the ZnTiMWW.
9. The micropowder of any of embodiments 1 to 8, wherein the ZnTiMWW contains titanium in an amount of from 1.0 to 2.0 weight-%, preferably of from 1.2 to 1.8 weight-%, more preferably of from 1.4 to 1.6 weight-%, calculated as Ti and based on the weight of the ZnTiMWW.
10. The micropowder of any of embodiments 1 to 9, having a crystallinity, as determined by X-ray diffraction (XRD) analysis, of at least 80%, preferably of at least 85%.
11. The micropowder of any of embodiments 1 to 10, comprising, based on the total weight of the micropowder and calculated as element, less than 0.001 weight-%, preferably less than 0.0001 weight-% of a noble metal, preferably selected from the group consisting of gold, silver, platinum, palladium, iridium, ruthenium, osmium, and a mixture of two or more thereof, more preferably selected from the group consisting of gold, platinum, gold, and a mixture of two or more thereof.
12. The micropowder of any of embodiments 1 to 11, comprising, based on the total weight of the micropowder and calculated as element, less than 0.1 weight.-%, preferably less than 0.01 weight-% of boron.
13. The micropowder of any of embodiments 1 to 12, having a bulk density of in the range of from 80 to 100 g/ml.
14. The micropowder of any of embodiments 1 to 13, being a spray powder, preferably obtainable or obtained by spray-drying.

Further, said ZnTiMWW catalyst in the form of a molding is preferably characterized by the following features and embodiments, including the combinations of embodiments according to the given dependencies:

1. A molding, comprising a microporous aluminum-free zeolitic material of structure type MWW containing titanium and zinc (ZnTiMWW), said molding preferably comprising a micropowder comprising, based on the weight of the micropowder, at least 95 weight-% of a microporous aluminum-free zeolitic material of structure type MWW containing titanium and zinc (ZnTiMWW), said molding more preferably comprising the micropowder according to any of the micropowder embodiments 1 to 14 as described hereinabove, the molding preferably further comprising at least one binder, preferably a silica binder.

2. The molding of embodiment 1, comprising mesopores having an average pore diameter in the range of from 4 to 40 nm, preferably from 20 to 30 nm as determined by Hg porosimetry according to DIN 66133.

3. The molding of embodiment 1 or 2, having a crystallinity, as determined by XRD analysis, of at least 55%, preferably in the range of from 55 to 75%.

4. The molding of any of embodiments 1 to 3, comprising the micropowder in an amount in the range of from 70 to 80 weight-% and the silica binder in an amount of from 30 to 20 weight-%, the micropowder together with the silica binder constituting at least 99 weight-% of the molding, wherein the molding has a concentration of silanol groups with respect to the total number of Si atoms of at most 6%, preferably at most 3%, as determined according to $^{29}$Si MAS NMR. The concentration of the silanol groups is understood as being determined according to Reference Example 3 of the present invention.

5. The molding of any of embodiments 1 to 4, being a strand having circular cross-section and a diameter in the range of from 1.5 to 1.7 mm and having a crush strength of at least 5 N, preferably in the range of from 5 to 20 N, more preferably in the range of from 12 to 20 N, the crush strength being determined by crush strength test machine Z2.5/TS1S according to the method as described in Reference Example 4 of the present invention.

6. The molding of any of embodiments 1 to 5, the $^{29}$Si-NMR spectrum of said molding comprising six peaks at the following position
   peak 1 at −98+/−x ppm,
   peak 2 at −104+/−x ppm,
   peak 3 at −110+/−x ppm,
   peak 4 at −113+/−x ppm,
   peak 5 at −115+/−x ppm,
   peak 6 at −118+/−x ppm,
with x in any of the peaks being 1.5, preferably 1.0, more preferably 0.5,
wherein Q which is defined as $Q=100*\{[a_1+a_2]/[a_4+a_5+a_6]\}/a_3$ is at most 1.6, preferably at most 1.4 and more preferably at most 1.3, with [$a_1+a_2$] being the sum of the peak areas of peaks 1 and 2, and [$a_4+a_5+a_6$] being the sum of the peak areas of peaks 4, 5, and 6, and $a_3$ being the peak area of peak 3. These $^{29}$Si-NMR characteristics are understood as being determined according the Reference Example 5 of the present invention.

7. The molding of any of embodiments 1 to 6, having a water uptake in the range of from 3 to 8 weight-%, preferably from 4 to 7 weight-%, more preferably from 4.5 to 6.5 weight-%. The water uptake is understood as being determined according to Reference Example 6 of the present invention.

8. The molding of any of embodiments 1 to 7, the infrared spectrum of said molding comprising a band in the region of 3746 cm$^{-1}$+/−20 cm$^{-1}$ and a band in the region of 3678 cm$^{-1}$+/−20 cm$^{-1}$, wherein the intensity ratio of the band in the region of 3746 cm$^{-1}$+/−20 cm$^{-1}$ relative to the band in the region of 3678 cm$^{-1}$+/−20 cm$^{-1}$ is at most 1.5, preferably at most 1.4, more preferably of at most 1.3, more preferably lower of at most 1.2. These IR characteristics are understood as being determined according the Reference Example 7 of the present invention.

A preferred process for the preparation of a preferred ZnTiMWW catalyst and the respective characterization of this ZnTiMWW catalyst is described in Reference Example 1 of the present invention.

Therefore, the present invention also relates to above-described process, wherein in (a), propene is reacted with hydrogen peroxide in the presence of a heterogeneous catalyst, said heterogeneous catalyst preferably comprising a zeolite, preferably a titanium zeolite, more preferably a titanium zeolite of structure type MWW (TiMWW), more preferably a zinc containing titanium zeolite of structure type MWW (ZnTiMWW).

Therefore, the process of the present invention preferably comprises (a) reacting propene, admixed with propane, with hydrogen peroxide in the presence of a heterogeneous catalyst, said heterogeneous catalyst preferably comprising a zeolite, preferably a titanium zeolite, more preferably a titanium zeolite of structure type MWW (TiMWW), more preferably a zinc containing titanium zeolite of structure type MWW (ZnTiMWW), in a reaction apparatus in the presence of acetonitrile as solvent, obtaining a stream S0 leaving the reaction apparatus, S0 containing propylene oxide, acetonitrile, water, at least one further component B, propane and optionally propene, wherein the normal boiling point of the at least one component B is higher than the normal boiling point of acetonitrile and wherein the decadic logarithm of the octanol-water partition coefficient (log $K_{OW}$) of the at least one component B is greater than zero.

Generally, the reaction in (a) can be carried out in any appropriate way. Thus, for example, it can be carried out in a batch reactor or in at least one semi-continuously operated reactor or in at least one continuously operated reactor. The continuous mode of operation is preferred, wherein the reaction is preferably carried out at a temperature in the range of from −10 to 120° C., more preferably from 30 to 90° C., more preferably from 30 to 65° C. Preferably, the temperature at which the reaction is carried out is not kept constant during the reaction but is adjusted continuously or step-wise to allow for a constant hydrogen peroxide conversion as determined in stream S0 leaving the reactor in which the epoxidation reaction in (a) is carried out. Preferably, the reaction in (a) is carried out in at least one continuously operated reactor such as a tube reactor or a tube bundle reactor which preferably contains at least one cooling jacket surrounding the at least one tube. If the reaction in (a) is carried out in such a reactor containing at least one cooling jacket, the term "reaction temperature" as used herein refers to the temperature of the cooling medium when entering the cooling jacket. Generally, due to catalyst deactivation, the reaction temperature is continuously or step-wise increased. Preferably, the reaction temperature is continuously or step-wise increased by 1° C./d at most, more preferably by less than 1° C./d. Preferably, the hydrogen peroxide conversion which is preferably kept constant is at least 80%, more preferably at least 85%, more preferably at least 90%, more preferably in the range of from 90 to 95%. The principle of a preferred hydrogen peroxide conversion determination is described in Example 1, section 1.1 a) hereinbelow. The pressures in the at least one reactor are generally in the range from 3 to 100 bar, preferably from 15 to 45 bar. In particularly preferred embodiments of the process of the present invention, the reaction is carried out at temperatures and pressures at which the reaction mixture is liquid and no gas phase is present in the at least one reactor wherein two or more liquid phases may exist. The molar ratio of propene relative to hydrogen peroxide with regard to the starting materials passed into the at least one reactor in which epoxidation is carried in (a) is preferably in the range of from 0.9:1 to 3.0:1, more preferably from 0.98:1 to 1.6:1, more preferably from 1.0:1 to 1.5:1. The amount of acetonitrile passed to the at least one reactor is adjusted so that the hydrogen peroxide concentration of the overall stream passed to the at least one reactor in which the epoxidation is carried out in (a) is preferably in the range of from 2 to 20 weight-%, more preferably from 5 to 12 weight-%, based on the total weight of the overall stream.

Preferably, the overall stream passed to the at least one epoxidation reactor, i.e. the reactor feed, contains of from 50 to 80 weight-%, more preferably from 60 to 70 weight-% acetonitrile, of from 7 to 14 weight-%, more preferably from 8 to 11 weight-% propene, of from 5 to 12 weight-%, more preferably from 6 to 10 weight-% hydrogen peroxide, and of from 10 to 25 weight-%, preferably from 12 to 20 weight-% water.

Preferably, the reaction in (a) is carried out in two or more stages, preferably in two or three stages, more preferably in two stages. Preferably, a two-stage reaction comprises:
   (a1) reacting propene, optionally admixed with propane, with hydrogen peroxide, preferably in the presence of a heterogeneous catalyst, said heterogeneous catalyst preferably comprising a zeolite, preferably a titanium zeolite, more preferably a titanium zeolite of structure type MWW (TiMWW), more preferably a zinc containing titanium zeolite of structure type MWW (Zn-TiMWW), in a reaction apparatus in the presence of acetonitrile as solvent, obtaining a stream S0-a1 leaving the reaction apparatus, S0-a1 containing propylene oxide, acetonitrile, water, optionally at least one further component B, optionally propane, optionally propene, and unreacted hydrogen peroxide;
   (a2) separating propylene oxide from S0-a1, obtaining a stream S0-a2-1 being enriched in propylene oxide and depleted of hydrogen peroxide, and a stream S0-a2-2 being depleted of propylene oxide and comprising unreacted hydrogen peroxide, acetonitrile, and water;
   (a3) subjecting the stream S0-a2-2, preferably after admixing with propene optionally admixed with propane, to epoxidation reaction conditions, preferably in the presence of a heterogeneous catalyst, said heterogeneous catalyst preferably comprising a zeolite, preferably a titanium zeolite, more preferably a titanium zeolite of structure type MWW (TiMWW), more preferably a zinc containing titanium zeolite of structure type MWW (ZnTiMWW), in a reaction apparatus obtaining a stream S0-a3 leaving the reaction apparatus, S0-a3 containing propylene oxide, acetonitrile, water, optionally at least one further component B, optionally propane, and optionally propene;
   wherein either S0-a1 and/or S0-a3 contain at least one further component B and wherein the normal boiling point of the at least one component B is higher than the normal boiling point of acetonitrile and wherein the decadic logarithm of the octanol-water partition coefficient (log $K_{OW}$) of the at least one component B is greater than zero.

In a preferred set-up of the process of the present invention as shown in FIG. 1 hereinbelow, the stream (5) is a preferred stream S0-a1, the stream (6) is a preferred stream S0-a2-1, the stream (7) is a preferred stream S0-a2-2, and the stream (9) is a preferred stream S0-a3. The stream (8) in FIG. 1 is a preferred stream of propene optionally admixed with propane which is preferably admixed in (a3).

Preferably, the streams S0-a2-1 and S0-a3 together constitute the stream S0 according to the present invention.

As far as the preferred epoxidation reaction conditions of stage (a1) are concerned, reference is made to the preferred epoxidation reaction as discussed above. The hydrogen peroxide can be separated off according to (a2) by any suitable methods. The hydrogen peroxide is preferably separated off by distillation using one or more distillation towers, preferably one distillation tower. This distillation tower is preferably operated at conditions allowing for obtaining a top stream which contains hydrogen peroxide in an amount of at most 100 weight-ppm, based on the total weight of the top stream, preferably containing essentially no hydrogen peroxide.

Additionally this distillation tower is preferably operated at conditions allowing for obtaining a top stream which contains at least 80%, more preferably at least 90% more preferably at least 95% of the propylene oxide contained in the feed stream S0-a1. Preferably, this distillation tower has of from 15 to 45, preferably from 20 to 40 theoretical trays and is operated at a pressure at the top of the tower in a range of from 0.5 to 1.2 bar, preferably from 0.7 to 1.1 bar. The reflux ratio of this distillation tower is preferably in the range of from 0.05:1 to 0.5:1, more preferably from 0.1:1 to 0.2:1. The bottoms stream obtained from the distillation tower in (a2), containing essentially all of the unreacted hydrogen peroxide from (a1) and further containing acetonitrile, water, is preferably passed to stage (a3). As far as stage (a3) is concerned, it is preferred to use an adiabatic reactor, preferably an adiabatic shaft reactor. The epoxidation conditions in (a3) are preferably chosen to allow for a hydrogen peroxide conversion at the outlet of (a3) of at least 99%, preferably at least 99.5%, more preferably at least 99.9% based on the hydrogen peroxide fed to (a1). In (a3), it is preferred to use the same catalyst as in (a1). As far as the propene is concerned which is preferably introduced into the reactor used in (a3), reference is made to the propene already discussed hereinabove in the context of (a). Thus, for example, chemical grade propene or polymer grade propene can be used, with polymer grade propene being preferred. If stages (a1) and (a3) are performed, the reactors are preferably operated so that the overall propene conversion, taking into account conversion in (a1) and conversion in (a3), is at least 65%, more preferably at least 70%, more preferably at least 75%.

Depending on the specific epoxidation conditions in (a), S0 may contain any conceivable amounts of propylene oxide, acetonitrile, water, the at least one further component B, optionally propene and optionally propane. Preferably, from 90 to 97 weight-%, more preferably from 92 to 97 weight-%, more preferably from 95 to 97 weight-% of S0 consist of acetonitrile, water, and propylene oxide, and from 0.01 to 3 weight-%, more preferably from 0.015 to 2 weight-%, more preferably from 0.02 to 0.1 weight-ppm of S0 consist of the at least one component B. The term " . . . weight-% of S0 consist of the at least one component B" refers to the overall amount of all components B contained in S0. More preferably, from 90 to 97 weight-%, more preferably from 92 to 97 weight-%, more preferably from 95 to 97 weight-% of S0 consist of acetonitrile, water, and propylene oxide, from 0.05 to 7 weight-%, more preferably from 0.1 to 6 weight-%, more preferably from 0.15 to 4 weight-% consist of propene and optionally propane, and wherein from 0.01 to 3 weight-%, preferably from 0.015 to 2 weight-%, more preferably from 0.02 to 1 weight-ppm of S0 consist of the at least one component B.

According to the present invention, the decadic logarithm of the octanol-water partition coefficient (log $K_{OW}$) of the at least one component B is greater than zero. The octanol-water partition coefficient (log $K_{OW}$) is a parameter well-known by the skilled person. For the sake of completeness, its definition and its determination are described in Reference Example 8 hereinbelow.

Typically, the at least one component B contained in S0 either is a by-product and/or a side-product obtained during the epoxidation reaction in (a), and/or is a compound which is formed during at least one of the work-up stages being preferably carried out downstream of (a) and which accumulates if certain process streams of the preferred integrated process are recycled into (a), and/or is contained as an impurity in at least one of the starting materials employed in (a) such as an impurity in the acetonitrile or an impurity in the hydrogen peroxide.

Preferably, the at least one component B is propionitrile, 1-nitropropane, 2-nitropropane, 3-methylbutanenitrile, n-pentanenitrile, 1-pentanol, 2-pentanol, 2-butanone, 2-pentanone, 2-hexanone, 4-methyl-2-heptanone, 2,6-dimethyl-4-heptanol, 4,6-dimethyl-2-heptanol, 2,6-dimethyl-4-heptanone, 4,6-dimethyl-2-heptanone, 2,6-dimethyl-4,6-heptandiol, 2,4-dimethyl-oxazoline, 2,5-dimethyloxazoline, cis-2,4-dimethyl-1,3-dioxolane, trans-2,4-dimethyl-1,3-dioxolane, acetaldehyde, propionaldehyde, 2-butanone at least one impurity contained in the hydrogen peroxide employed in (a), or a combination of two or more of these compounds.

Preferably, the at least one component B includes propionitrile, 1-nitropropane, 2-nitropropane, 2,6-dimethyl-4-heptanol, 4,6-dimethyl-2-heptanol, 2,6-dimethyl-4-heptanone, acetaldehyde, propionaldehyde, 2-butanone, or a combination of two or more of these compounds. More preferably, the at least one component B includes a combination of three or more of these compounds, more preferably a combination of four or more of these compounds, more preferably a combination of five or more of these compounds. More preferably, the at least one component B includes a combination of propionitrile, 1-nitropropane, 2-nitropropane, 2,6-dimethyl-4-heptanol, 4,6-dimethyl-2-heptanol, and 2,6-dimethyl-4-heptanone. Also preferably, the at least one component B includes a combination of seven or more of these compounds, more preferably a combination of eight or more of these compounds. More preferably, the at least one component B includes a combination of propionitrile, 1-nitropropane, 2-nitropropane, 2,6-dimethyl-4-heptanol, 4,6-dimethyl-2-heptanol, 2,6-dimethyl-4-heptanone, acetaldehyde, and propionaldehyde. Also preferably, the at least one component B includes a combination of nine or more of these compounds. More preferably, the at least one component B includes a combination of propionitrile, 1-nitropropane, 2-nitropropane, 2,6-dimethyl-4-heptanol, 4,6-dimethyl-2-heptanol, 2,6-dimethyl-4-heptanone, acetaldehyde, propionaldehyde, and 2-butanone.

Regarding the at least one impurity contained in the hydrogen peroxide employed in (a), this at least one impurity is preferably an alkyl phosphate such as tris-(2-ethylhexyl) phosphate, a nonyl alcohol such as diisobutylcarbinol, an alkylcyclohexanol ester such as 2-methylcyclohexylacetate, an N,N-dialkyl carbonamide such as N,N-dibutylpropionamide, an N-alkyl-N-aryl carbonamide such as N-ethyl-N-phenylbenzamide, an N,N-dialkyl carbamate such as 2-ethylhexyl-N-butylcarbamate, a tetraalkyl urea such as tetra-n-butylurea, a cycloalkyl urea such as dihexyl propeneurea, a phenylalkyl urea such as N,N-dibutyl-N'-methyl-N'-phenylurea, an N-alkyl-2-pyrrolidone such as octyl pyrrolidone, an N-alkyl caprolactam such as n-octyl caprolactam, $C_8$-$C_{12}$ alkyl aromatic compounds, dibutyl amine, dibutyl formamide, 1-butanol, butyric aldehyde, 2-ethylhexanol, 2-ethylanthraquinone, 2-ethyl-5,6,7,8-tetrahydroanthra-quinone, or a combination of two or more of these compounds.

It is conceivable that the reacting propene, admixed with propane, with hydrogen peroxide in the presence of a heterogeneous catalyst, said heterogeneous catalyst preferably comprising a zeolite, preferably a titanium zeolite, more preferably a titanium zeolite of structure type MWW (TiMWW), more preferably a zinc containing titanium zeolite of structure type MWW (ZnTiMWW), in a reaction apparatus in the presence of acetonitrile as solvent, such as reacting propene in (a1) and/or (a3), is carried out in the presence of at least one potassium salt which is dissolved in the respective mixtures which are subjected to epoxidation conditions in (a), such as in (a1) and/or (a3). Preferably, the at least one potassium salt is selected from the group consisting of at least one inorganic potassium salt, at least one organic potassium salt, and combinations of at least one inorganic potassium salt and at least one organic potassium salt, wherein preferably at least one of the at least one potassium salt is an organic potassium salt. More preferably, the at least one potassium salt is selected from the group consisting of at least one inorganic potassium salt selected from the group consisting of potassium hydroxide, potassium halides, potassium nitrate, potassium sulfate, potassium hydrogen sulfate, potassium perchlorate, dipotassium hydrogen phosphate, potassium dihydrogen phosphate, at least one organic potassium salt selected from the group consisting of potassium salts of aliphatic saturated monocarboxylic acids preferably having 1, 2, 3, 4, 5 or 6 carbon atoms, potassium carbonate, and potassium hydrogen carbonate, and a combination of at least one of the at least one inorganic potassium salts and at least one of the at least one organic potassium salts. More preferably, the at least one potassium salt is selected from the group consisting of at least one inorganic potassium salt selected from the group consisting of potassium hydroxide, potassium chloride, potassium nitrate, at least one organic potassium salt selected from the group consisting of potassium formate, potassium acetate, potassium carbonate, and potassium hydrogen carbonate, and a combination of at least one of the at least one inorganic potassium salts and at least one of the at least one organic potassium salts.

Therefore, the present invention also relates to a process wherein (a) comprises reacting propene, optionally admixed with propane, with hydrogen peroxide in a reaction apparatus in the presence of acetonitrile as solvent and in the presence of at least one dissolved potassium salt, obtaining a stream S0 leaving the reaction apparatus, S0 containing propylene oxide, acetonitrile, water, at least one further component B, optionally propene and optionally propane, wherein the normal boiling point of the at least one component B is higher than the normal boiling point of acetonitrile and wherein the decadic logarithm of the octanol-water partition coefficient (log $K_{OW}$) of the at least one component B is greater than zero.

Step (b)

According to step (b) of the process of the present invention, propylene oxide is separated from S0, and a stream S1 is obtained which, compared to S0, is depleted of propylene oxide and which contains acetonitrile, water and the at least one further component B. If S0 additionally contains propene and/or propane, it is preferred that the propene and/or the propane are also separated from S0 to obtain a stream S1 is obtained which, compared to S0, is depleted of propylene oxide, propene and/or propane, and which contains acetonitrile, water and the at least one further component B. Further, if S0 additionally contains oxygen, it is preferred that the oxygen is also separated from S0 a stream S1 is obtained which, compared to S0, is depleted of propylene oxide and oxygen and which contains acetonitrile, water and the at least one further component B. Preferably, S0 obtained according to the process of the present invention contains propene, propane, and optionally oxygen, and apart from propylene oxide, propene, propane and optionally oxygen are separated from S0 to obtain S1 which, compared to S0, is depleted of propylene oxide, propene and propane and optionally oxygen, and which contains acetonitrile, water and the at least one further component B.

Regarding the separation of the propene and/or the propane, and/or the oxygen from S0, no specific restrictions exist. In particular, all conceivable sequences of separation of the individual components and all conceivable separation techniques such as distillation are possible. Therefore, it is conceivable to separate the propene and/or the propane and optionally the oxygen together with propylene oxide from S0 to obtain S1. The separated stream enriched in propene and/or propane and optionally oxygen is then preferably subjected to suitable separation stages and/or work-up stages from which a stream is obtained which essentially consists of propylene oxide as valuable product. Preferably, the stream S0 is subjected to a first separation stage where propene and optionally propane are separated. If S0 additionally contains oxygen, it is preferred that the oxygen is separated together with the propene and/or the propane.

Therefore, the present invention relates to the process as described above, comprising (b) separating propylene oxide from S0, after having separated propene and optionally propane, obtaining a stream S1 containing acetonitrile, water and the at least one further component B. Also, the present invention relates to the process as described above, comprising (b) separating propylene oxide from S0, after having separated propene and propane, obtaining a stream S1 containing acetonitrile, water and the at least one further component B. Also, the present invention relates to the process as described above, comprising (b) separating propylene oxide from S0, after having separated propene, propane, and optionally oxygen, obtaining a stream S1 containing acetonitrile, water and the at least one further component B. Also, the present invention relates to the process as described above, comprising (b) separating propylene oxide from S0, after having separated propene, propane, and oxygen, obtaining a stream S1 containing acetonitrile, water and the at least one further component B.

Therefore, it is preferred that step (b) of the process of the present invention comprises a step (I) wherein propene, optionally together with propane, and oxygen which is optionally additionally contained in S0, are separated from S0 to obtain a stream S01 enriched in propylene oxide, acetonitrile, water, and the at least one component B which stream S01 is depleted of propene, optionally propane, and oxygen; and further comprises a step (II) wherein propylene oxide is separated from S01, obtaining a stream S02 enriched in acetonitrile, water and the at least one component B which stream S02 is depleted of propylene oxide.

Regarding to separation in (I), no specific restrictions exist. Preferably, the separation is carried out so that at least 90 weight-%, more preferably at least 95 weight-%, more preferably at least 98 weight-%, more preferably at least 99 weight-% of S01 consist of acetonitrile, water, the at least one component B and propylene oxide. Preferably, a fractionation unit is employed for the separation in (I). Further preferably, the separation in (I) is carried out in at least one distillation tower, more preferably in one distillation tower. From this distillation tower, S01 is preferably obtained as bottoms stream. Preferably, this distillation tower has from 10 to 30, more preferably from 15 to 25 theoretical trays. The distillation tower is preferably operated at a top pressure of from 0.5 to 1.2 bar, more preferably of from 0.7 to 1.1 bar. In order to facilitate said separation task, it was found that it is advantageous to add either liquid acetonitrile or a liquid mixture of acetonitrile with water to the top of the column. It is believed that this external reflux serves as entraining agent which, among others, prevents propylene oxide from being separated via the top of the distillation tower. According to a preferred embodiment of the present invention, a portion of the bottom stream of the distillation tower preferably employed in stage (II) is used. It is also conceivable that the stream TL2 described hereinbelow or a portion thereof is used as entraining agent. The amount of TL2 will not be sufficient, and another stream is to be added. Preferably, the weight ratio of the amount of acetonitrile fed as external reflux to the top of the distillation tower relative to the weight of the stream S0 fed into the distillation tower and to be separated in the distillation tower is in the range of from 1:1 to 4:1 preferably from 1.5:1 to 3:1. The temperature of the external reflux is generally in the range of from 2 to 20° C., preferably in the range of from 5 to 15° C. According to the present invention, preferably at least 85 volume-%, more preferably at least 90 volume-%, more preferably at least 93 volume-% of the top stream of the distillation column according to (I) consist of propene, oxygen, and optionally propane. Depending on its oxygen content, this top stream can be passed to a further suitable workup stage wherein the oxygen content is suitably decreased in order to allow, e.g., for recycling the oxygen-depleted stream to be recycled to one or more stages of the present invention, such as a starting material for stage (a) of the inventive process like stage (a1) or stage (a3), or as portion of the stream P described hereinbelow. If the oxygen content of said top stream is reduced, it is preferred to reduce the oxygen by reaction with hydrogen in the presence of a suitable catalyst. Such catalysts are, for example, catalysts comprising tin and at least one noble metal as described in WO 2007/000396 A1, in particular in Example 1 of WO 2007/000396 A1. It is also conceivable to use catalysts comprising copper in elemental and/or oxidic form on a support, wherein copper is present on the support in an amount of 30 to 80 weight-% based on the whole catalyst and calculated as CuO. Such catalysts can be prepared, for example, according to the example of EP 0 427 062 A2, catalyst 2, page 4, lines 41 to 50 (corresponding to U.S. Pat. No. 5,194,675). In order to reduce the oxygen content, also other suitable methods are conceivable. Optionally, said top stream, prior to be subjected to hydrogenation, can be compressed and partially condensed wherein a liquid stream is obtained which essentially consists of propene and optionally propane and acetonitrile and which contains minor amounts of water. The non-condensed portion essentially consists of propene and optionally propane and oxygen and contains a minor amount of water wherein, compared to the basic stream, the oxygen content is increased while still being in a range so that the mixture is not ignitable. This oxygen-enriched stream is then subjected to hydrogenation.

As mentioned above, prior to using the stream S01 as stream S1 according to the present invention, it is especially preferred to separate propylene oxide from S01 in (II) to obtain a stream S02 which is essentially free of propylene oxide. Regarding to separation in (II), no specific restrictions exist. Preferably, the separation is carried out so that preferably at least 90 weight-%, more preferably at least 95 weight-%, more preferably at least 99 weight-% of S02 consist of acetonitrile, water and the at least one component B. More preferably, the weight ratio of acetonitrile relative to water in S02 is greater than 1:1, preferably in the range of from 2:1 to 10:1, more preferably from 2.5:1 to 5:1. Preferably, a fractionation unit is employed for the separation in (II). Further preferably, the separation in (II) is carried out in at least one distillation tower, more preferably in one distillation tower. Preferably, this tower has of from 50 to 80, more preferably of from 60 to 70 theoretical trays. The distillation tower is preferably operated at a top pressure of from 0.2 to 2 bar, more preferably of from 0.4 to 1 bar. Optionally, at least one suitable polar solvent or a mixture of two or more polar solvents, preferably water, can be added in the upper part of the column as extractive agent. According to an embodiment of the process of the present invention, the separation according to stage (III) can be carried out by introducing S01 into an extractive distillation column;
additionally introducing a polar extracting solvent or a mixture of two or more thereof, preferably water, into said extractive distillation column;
distilling propylene oxide overhead from said extractive distillation column as top stream, wherein the top stream comprises only minor amounts of acetonitrile such as 500 ppm or less;
compressing said top stream obtained overhead in the previous step by means of at least one compressor to give a compressed vapor;
condensing the compressed vapor obtained in the previous step and returning at least part of the heat of condensation to at least one reboiler employed in the extractive distillation column.

From this distillation tower according to (II), a top stream is obtained which contains at least 90 weight-%, preferably at least 95 weight-%, more preferably at least 99 weight-% of propylene oxide. Further from this distillation tower, S02 is preferably obtained as bottoms stream which preferably contains 500 weight-ppm at most, preferably 100 weight-ppm at most, and more preferably 60 weight-ppm at most of propylene oxide, based on the weight of S02.

Depending on the requirements on the propylene oxide quality, it is conceivable to use this propylene oxide fraction without any further purification. It is, however, also conceivable to further purify said propylene oxide fraction, for example in at least one further distillation stage.

From the distillation tower according to (II) or optionally from the further distillation stage, a propylene oxide stream is obtained wherein at least 99.5 weight-%, more preferably at least 99.9 weight-%, more preferably at least 99.999 weight-% of said stream consist of propylene oxide. Therefore, the present invention also relates to a composition comprising at least 99.999 weight-% of propylene oxide, obtainable or obtained by a process as described above and comprising the separation stage (II).

Thus, the present invention preferably relates to the process as described above, wherein (b) comprises
(I) separating propene, optionally together with propane, and oxygen which is optionally additionally contained in S0, from S0, obtaining a stream S01 enriched in propylene oxide, acetonitrile, water, and the at least one component B, wherein preferably at least 99 weight-% of S01 consist of acetonitrile, water, the at least one component B and propylene oxide; wherein for separation, preferably a fractionation unit is used, wherein preferably, at the top of the fractionation unit, liquid acetonitrile, optionally admixed with liquid water, is added as entraining agent;
(II) separating propylene oxide from S01, obtaining a stream S02 enriched in acetonitrile, water and the at least one component B, wherein preferably at least 95 weight-% of S02 consist of acetonitrile, water and the at least one component B, and wherein the weight ratio of acetonitrile relative to water is greater than 1:1.

Preferably, S02 obtained from step (b), preferably from step (II) comprised in (a), is subjected to step (c) as stream S1.

Preferably, from 90 to 99.9 weight-%, more preferably from 95 to 99.8 weight-%, more preferably from 99 to 99.7 weight-% of S1 consist of acetonitrile and water, and preferably from 0.01 to 5 weight-%, more preferably from 0.015 to 3 weight-%, more preferably from 0.02 to 2 weight-% of S1 consist of the at least one component B.

Optionally, at least a portion of S02 is diverted and used as entraining agent in the fractionation unit according to (I) as described above. Preferably, if used as entraining agent, from 15 to 35%, more preferably from 20 to 35% of S02 are diverted and preferably added at the top of the fractionation unit used in (I).

Optional Additional Step(s) Comprised in (b)

Depending on the specific conditions during the upstream stages of the process of the present invention, namely stages (a), (I) and (II), the bottoms stream obtained from the distillation tower according to (II) may also contain certain amounts of hydroperoxides such as certain amounts of hydrogen peroxide and/or certain amounts of organic hydroperoxides, for example, 1-hydroperoxypropanol-2 and/or 2-hydroperoxypropanol-1. Preferably, the bottoms stream obtained from the distillation tower according to (III) may contain at most 2 weight-%, more preferably at most 1 weight-% of these hydroperoxides in total, based on the weight of the bottoms stream. In order to reduce the hydroperoxide content and, thus, to avoid the build-up of the hydroperoxides which are believed to possibly have a detrimental influence as far as the formation of undesirable by-products and safety aspects based on the decomposition of the hydroperoxides are concerned, it is conceivable to subject said bottoms stream obtained from the distillation tower according to (II) to at least one further process stage. Said build-up especially occurs if the inventive highly integrated process is realized. While every suitable method for at least partially removing these hydroperoxides is conceivable, it is especially preferred to catalytically reduce, preferably to catalytically hydrogenate the hydroperoxides. As suitably catalyst, a catalyst may be mentioned which is described in US 2004068128 A1, in particular in paragraphs [0053] to [0076]. Preferred catalysts are selected from the group consisting of heterogeneous catalysts comprising Ru, Ni, Pd, Pt, either individually or as a mixture of two or more thereof, as active metal on a suitable support material. An especially suitable catalyst, namely a supported catalyst comprising 5 weight-% of Pd on activated carbon is, described in Example E2 of US 2004068128 A1. The pressure during hydrogenation is typically in the range of from 1 to 100 bar(abs), preferably from 1 to 10 bar(abs), and the temperature during hydrogenation is typically in the range of from 0 to 180° C., preferably from 25 to 120° C., more preferably from 65 to 85° C. The hydrogen partial pressure during hydrogenation is preferably in the range of from more than 1 to 20 bar, more preferably from 2 to 15 bar, more preferably from 3 to 13 bar. If the hydrogenation is carried out in a fixed bed, which is preferred, the residence time of the liquid passed through the hydrogenation reactor is generally in the range of from 1 second (s) to 1 hour (h), preferably from 10 s to 20 minutes (min), in particular from 30 s to 5 min. Depending on the reaction conditions employed for reducing, preferably hydrogenating the bottoms stream obtained from the distillation tower according to (II), it may be necessary to separate the resulting stream from the catalyst, preferably hydrogenation catalyst and/or non-reacted reducing agent, preferably hydrogen and/or by-products from the hydrogenation, preferably CO and/or methane. In particular, the stream resulting from reduction, preferably hydrogenation, contains at least 95 weight-% acetonitrile and water, based on the total weight of the bottoms stream, wherein the weight ratio of acetonitrile relative to water is preferably greater than 1:1. Generally, it is conceivable to use this stream obtained from the hydrogenation and preferably separation of the catalyst as stream S1 of the present invention.

Depending on the specific conditions during the upstream stages of the present invention, i.e. stages (a), (I) and (II), and the reduction, preferably the hydrogenation stage, the stream obtained from reduction, preferably hydrogenation may contain certain amounts of acetaldehyde and optionally further low boilers such as, for example, propionaldehyde and acetone. Typically, this stream may contain up to 2000 weight-ppm, preferably up to 1000 weight-ppm, more preferably up to 300 weight-ppm of acetaldehyde and other low-boilers in total, based on the total weight of this stream. In order to reduce the acetaldehyde content and optionally the content with respect to the other low boilers and, thus, to avoid the build-up of these compounds which especially occurs if the inventive highly integrated process is realized, it is preferred to subject this stream to at least one further process stage. While every suitable method for at least partially removing acetaldehyde is conceivable, it is especially preferred to separate acetaldehyde at least partially from the stream by distillation. Separation according to this stage is preferably carried out in at least one distillation tower, more preferably in one distillation tower. Preferably, this tower has of from 15 to 40, more preferably of from 20 to 35 theoretical trays. The distillation tower is preferably operated at a top pressure in the range of from 0.7 to 2 bar, more preferably from 1.1 to 2 bar.

From this distillation tower, a bottoms stream is obtained which preferably contains 200 weight-ppm at most, preferably 100 weight-ppm at most, more preferably 50 weight-ppm at most of acetaldehyde and other low boilers in total, based on the weight of the bottoms stream. Preferably, at least 98 weight-%, more preferably at least 98.5 weight-%, more preferably at least 98.7 weight-% of the bottoms stream consist of acetonitrile, water, and the at least one component B. Preferably, at least 98 weight-%, more preferably at least 98.5 weight-%, more preferably at least 98.7 weight-% of the bottoms stream consist of acetonitrile, water and the at least one component B, and wherein the weight ratio of acetonitrile relative to water is greater than 1:1. Generally, it is conceivable to use this bottoms stream as stream S1 in the process of the present invention. According to a conceivable embodiment of the present invention, no such distillation stage is performed.

Therefore, the present invention also relates to the process as described above, wherein (b) further comprises
(IIIa) subjecting S02 obtained from (II) to hydrogenation; and/or
(IIIb) subjecting the stream obtained from (II) or (IIIa) to distillation to obtain a bottoms stream, wherein the hydrogenated stream obtained from (IIIa) or the bottoms stream obtained from (IIIb) is subjected to (c) as S1.

Thus, the present invention also relates to the process as described above, wherein (b) further comprises
(IIIa) subjecting the stream obtained from (II) to hydrogenation, obtaining stream S1 and subjecting S1 to step (c).

Thus, the present invention also relates to the process as described above, wherein (b) further comprises
(IIIb) subjecting the stream obtained from (II) to a distillation stage, preferably carried out in a distillation column operated at a top pressure of from 0.7 to 2 bar, more preferably of from 1.1 to 2 bar, to obtain stream S1 and subjecting S1 to step (c).

Also, the present invention relates to the process as described above, wherein (b) further comprises
(IIIa) subjecting the stream S02 obtained from (II) to a hydrogenation stage, preferably to a catalytical hydrogenation stage, the catalyst preferably being a heterogeneous catalysts comprising Ru, Ni, Pd, Pt, either individually or as a mixture of two or more thereof, as active metal on a suitable support material, in particular Pd on activated carbon; said hydrogenation preferably being carried out at a pressure during hydrogenation in the range of from 1 to 100 bar(abs), preferably from 1 to 10 bar(abs), and a temperature during hydrogenation in the range of from 0 to 180° C., preferably from 25 to 120° C., more preferably from 65 to 85° C.;
(IIIb) subjecting the stream obtained from (IIIa) to a distillation stage, preferably carried out in a distillation column operated at a top pressure of from 0.7 to 2 bar, more preferably of from 1.1 to 2 bar, to obtained stream S1 and subjecting S1 to step (c).

As mentioned above, it is preferred that the stage (b) of the process of the present invention neither comprises (IIIa) nor (IIIb).

Step (c)

According to step (c) of the process of the present invention, the stream S1 is divided into two streams S2 and S3 wherein the stream S3 is subjected, as the part-stream of the present invention, to step (d) as discussed hereinunder. The term "is divided into two streams" as used in this context of the present invention generally encompasses embodiments according to which the stream S1 is divided into more than two streams provided that the streams S2 and S3 as defined herein are obtained. No specific restrictions exist which portion of S1 is separated as S3. Preferably, the total weight of S3 relative to the total weight of S1 is less than 50%, more preferably less than 40%, more preferably less than 30%. More preferably, the total weight of S3 relative to the total weight of S1 is at least 0.01%. More preferably, the total weight of S3 relative to the total weight of S1 is in the range of from 0.01 to 25%. More preferably, the total weight of S3 relative to the total weight of S1 is in the range of from 0.05 to 20%, preferably from 0.1 to 15%, more preferably from 0.2 to 10%, more preferably from 0.5 to 7.5%. Preferred conceivable ranges are from 0.5 to 1.5% or from 1.0 to 2.0% or from 1.5 to 2.5% or from 2.0 to 3.0% or from 2.5 to 3.5% of from 3.0 to 4.0% or from 3.5 to 4.5% or from 4.0 to 5.0% or from 4.5 to 5.5% or from 5.0 to 6.0% or from 5.5 to 6.5% or from 6.0 to 7.0% or from 6.5 to 7.5%.

Step (d)

According to step (d) of the process of the present invention, the stream S3 is subjected to a vapor-liquid fractionation in a first fractionation unit, obtaining a vapor fraction stream S4a being depleted, relative to S3, of at least one of the at least one component B and obtaining a liquid bottoms stream S4b, wherein at least part of the vapor fraction stream S4a is subjected to a vapor-liquid fractionation in a second fractionation unit, obtaining a vapor fraction stream S4c and a liquid bottoms stream S4 being depleted, relative to S4a, of at least one of the at least one component B.

Generally, it was found that using for the impurity separation according to the present invention a fractionation unit comprising one single distillation column, already leads to excellent results with regard to most of the impurities. However, it was found that in view of the complexity of the spectrum of the impurities comprised in stream S1, although comprised only in traces, even better results are obtained when two serially coupled fractionation units are used. In particular, it was found that while the first fractionation unit is especially useful to separate impurities having a comparatively high boiling point, including, for example, propionitrile, 1-nitropropane, 2-nitropropane, 2,6-dimethyl-4-heptanol, 4,6-dimethyl-2-heptanol, and/or 2,6-dimethyl-4-heptanone, the second fractionation unit is especially useful to separate impurities having a comparatively high boiling point, including, for example acetaldehyde, propionaldehyde or 2-butanone. Thus, using the two serially coupled fractionation units, it was possible to separate essentially all impurities which, when accumulating in the course of a continuous process for preparing propylene oxide, tend to have a negative influence on the performance of the heterogeneous catalyst which is preferably employed in the epoxidation process, in particular a zeolite-based catalyst having framework structure MWW and containing Ti.

Therefore, the present invention relates to the process as described above, wherein in (d), the stream S3 is subjected to a vapor-liquid fractionation in a first fractionation unit, obtaining a vapor fraction stream S4a being depleted, relative to S3, of at least one of the at least one component B, the at least one of the at least one component B comprising propionitrile, or 1-nitropropane, or 2-nitropropane, or 2,6-dimethyl-4-heptanol, or 4,6-dimethyl-2-heptanol, or 2,6-dimethyl-4-heptanone, or a combination of two, three, four, five, or six thereof, and obtaining a liquid bottoms stream S4b, wherein at least part of the vapor fraction stream S4a is subjected to a vapor-liquid fractionation in a second fractionation unit, obtaining a vapor fraction stream S4c and a liquid bottoms stream S4 being depleted, relative to S4a, of at least one of the at least one component B, the at least one of the at least one component B comprising acetaldehyde, or propionaldehyde, or 2-butanone, or a combination of two or three thereof.

The term "S4a being depleted, relative to S3, of at least one of the at least one component B" as used in this context of the present invention relates to a stream S4a in which the amount of the at least one of the at least one component B is lower than the respective amount of the at least one of the at least one component B in stream S3. The term "S4 being depleted, relative to S4a, of at least one of the at least one component B" as used in this context of the present invention relates to a stream S4 in which the amount of the at least one of the at least one component B is lower than the respective amount of the at least one of the at least one component B in stream S4a.

Further, the present invention relates to the process as described above, wherein in (d), the stream S3, comprising propionitrile, 1-nitropropane, 2-nitropropane, 2,6-dimethyl-4-heptanol, 4,6-dimethyl-2-heptanol, 2,6-dimethyl-4-heptanone, or a combination of two, three, four, five, or six thereof, and further comprising acetaldehyde, or propionaldehyde, or 2-butanone, or a combination of two or three thereof, is subjected to a vapor-liquid fractionation in a first fractionation unit, obtaining a vapor fraction stream S4a being depleted, relative to S3, of propionitrile, or 1-nitropropane, or 2-nitropropane, or 2,6-dimethyl-4-heptanol, or 4,6-dimethyl-2-heptanol, or 2,6-dimethyl-4-heptanone, or a combination of two, three, four, five, or six thereof, and obtaining a liquid bottoms stream S4b, wherein at least part of the vapor fraction stream S4a is subjected to a vapor-liquid fractionation in a second fractionation unit, obtaining a vapor fraction stream S4c and a liquid bottoms stream S4 being depleted, relative to S4a, of acetaldehyde, or propionaldehyde, or 2-butanone, or a combination of two or three thereof.

In particular, it was found that if the configuration of the two serially coupled fractionation units is used, that in addition to the impurities having a comparatively high boiling point, including, for example, propionitrile, 1-nitropropane, 2-nitropropane, 2,6-dimethyl-4-heptanol, 4,6-dimethyl-2-heptanol, and/or 2,6-dimethyl-4-heptanone, other compound having a comparatively low boiling point including, for example, acetaldehyde, propionaldehyde or 2-butanone, can be suitably separated from S3, wherein, relative to S3, the respective amount of such a compound in S4 is in the range of from 10 to 70%, preferably from 15 to 60%.

Generally, no specific restrictions exist regarding step (d) provided that a liquid bottoms stream S4 is obtained which is depleted of the at least one component B and which can be fed back into the process of the present invention. Surprisingly, however, it was found that it is especially preferred if the acetonitrile concentration of the liquid bottoms stream S4b is in a specific range. This specific range was found to allow to keep the acetonitrile concentration in the liquid bottoms stream S4b as low as possible, thus avoiding too high a loss of acetonitrile, and simultaneously to separate a very high amount of the at least one component B via the liquid bottoms stream S4b. This specific range of the concentration of the acetonitrile in the liquid bottoms stream S4b obtained in (d) may be from 1 to 50 weight-%, from 2 to 45 weight-%, or from 5 to 40 weight-%. Preferably, in (d), vapor-liquid fractionation is carried out in the first fractionation unit so that from 10 to 30 weight-%, preferably from 10 to 25 weight-% of the liquid bottoms stream S4b consist of acetonitrile. More preferably, in (d), vapor-liquid fractionation is carried out in the first fractionation unit so that from 10 to 30 weight-%, preferably from 10 to 25 weight-% of the liquid bottoms stream S4b consist of acetonitrile and from 0.1 to 10 weight-%, preferably from 0.25 to 5 weight-% of the liquid bottoms stream S4b consist of the at least one further component B.

Therefore, the present invention preferably relates to the process as described above, wherein in (c), the total weight of S3 relative to the total weight of S1 is in the range of from 0.5 to 7.5% and wherein in (d), vapor-liquid fractionation is carried out in the first fractionation unit so that from 10 to 25 weight-% of the liquid bottoms stream S4b consist of acetonitrile. More preferably, the present invention relates to the process as described above, wherein in (c), the total weight of S3 relative to the total weight of S1 is in the range of from 0.5 to 7.5% and wherein in (d), vapor-liquid fractionation is carried out in the first fractionation unit so that from 10 to 25 weight-% of the liquid bottoms stream S4b consist of acetonitrile and from 0.25 to 5 weight-% of the liquid bottoms stream S4b consist of the at least one further component B.

Generally, no specific restrictions exist how the vapor-liquid fractionation is carried out in the first fractionation unit provided that the above-mentioned acetonitrile concentration in the liquid bottoms stream S4b are achieved. In particular, the pressure and/or the temperature and/or the number of the theoretical trays of the fractionation unit and/or the reflux ratio will be suitably adjusted by the skilled person.

Preferably in (d), vapor-liquid fractionation is carried out in the first fractionation unit at an absolute pressure at the top of the first fractionation unit in the range of from 0.5 to 5 bar, more preferably from 0.75 to 2 bar, more preferably from 1 to 1.5.

Preferably, in (d), the number of theoretical trays of the first fractionation unit is in the range of from 1 to 100, more preferably from 2 to 25, more preferably from 3 to 10.

According to a conceivable embodiment of the present invention, the first fractionation unit in (d) is operated with reflux. While it is generally possible to use any suitable stream as reflux, it may be preferred to use a portion of S4a, preferably after condensation, as reflux. The reflux ratio may be in the range of from 0.01:1 to 10:1, such as from 0.1:1 to 5:1, or from 0.5:1 to 2:1. The term "reflux ratio" as used in this context is defined as the ratio of the reflux flow relative to S4a and is a measure of how much of the material going up the top of the first fractionation unit is returned back to the first fractionation unit as reflux.

According to a preferred embodiment of the present invention, the first fractionation unit in (d) is operated without reflux. According to this embodiment, it is preferred to feed the stream S3 to the top of the first fractionation unit. In this case, it is generally possible to operate the first fractionation unit as a reboiled stripping unit or as a non-reboiled stripping unit. If the first fractionation unit is designed as a reboiled stripping unit, it is preferred that at least one heat exchanger is suitably arranged at the bottoms of the first fractionation unit in order to allow for the evaporation of the bottoms stream of the first fractionation unit wherein the stripping vapor is generated internally. If the first fractionation unit is designed as a non-reboiled stripping unit, it is preferred that at least one external vapor feed stream is employed as stripping vapor and to omit the at least one heat exchanger arranged at the bottoms of the first fractionation unit. Generally, it is possible to combine at least one heat exchanger arranged at the bottoms of the first fractionation unit and at least one external vapor feed stream. Preferably, in case the first fractionation unit is operated without reflux, the first fractionation unit is operated as a reboiled stripping unit.

Generally, from 1 to 10%, preferably from 2 to 5% of the stream S3 subjected to the first fractionation unit are removed via the liquid bottoms stream S4b. The liquid bottoms stream S4b obtained from the first fractionation unit according to (d) generally can be subjected to further work-up stages. For example, it is possible to suitably separate acetonitrile from S4b. Further, it may be possible that the liquid bottoms stream comprises or consists of two liquid phases wherein the lower phase which essentially consists of acetonitrile and water can be worked-up to minimize acetonitrile losses in the course of step (d). If present, the upper organic phase usually made up less than 10 weight-% of the total amount of the bottoms stream. Preferably, the liquid bottoms stream S4b, optionally after further acetonitrile separation, is discarded, and since S3 divided from S2 preferably constitutes only a minor portion of S2 which minor portion surprisingly effectively prevents the build-up of the concentration of the at least one component B in the highly integrated process of the present invention, and since only a minor portion of S3 is removed via S4b, simply discarding S4b even without any further work-up is economically advantageous.

Preferably in (d), at least 75 weight-%, more preferably at least 80 weight-%, more preferably at least 85 weight-%, more preferably at least 90 weight-% of the vapor fraction stream S4a are subjected to the vapor-liquid fractionation in the second fractionation unit. More preferably in (d), 95 to 100 weight-%, more preferably from 99 to 100 weight-%, more preferably from 99.9 to 100 weight-% of the vapor fraction stream S4a are subjected to the vapor-liquid fractionation in the second fractionation unit. More preferably, the vapor fraction stream S4a obtained from the first fractionation unit is completely subjected to the vapor-liquid fractionation in the second fractionation unit.

While it is generally possible to condense at least part of the vapor fraction stream S4a before it is subjected to the second fractionation unit, it is preferred not to condense the vapor fraction stream S4a before it is subjected to the second fractionation unit.

Generally, there are no specific restrictions where the at least part of stream S4a is fed to the second fractionation unit. Preferably, the at least part of stream S4a is fed to the lower part of the second fractionation unit, preferably to the bottoms of the second fractionation unit.

Preferably, the second fractionation unit is operated at an absolute pressure in the bottom of the second fractionation unit in the range of from 65 to 95%, more preferably from 70 to 90, more preferably from 75 to 85% of the pressure at the top of the first fractionation unit Therefore, the present invention relates to the process as defined above, wherein S3 is fed to the top of the first fractionation unit and the at least part of the vapor fraction stream S4a is fed to the bottom of the second fractionation unit, wherein in (d), the first fractionation unit is operated at an absolute pressure at the top of the first fractionation unit in the range of from 0.5 to 5 bar, preferably from 0.75 to 2 bar, more preferably from 1 to 1.5 bar, and wherein the second fractionation unit is operated at an absolute pressure in the bottom of the second fractionation unit in the range of from 65 to 95%, preferably from 70 to 90, more preferably from 75 to 85% of the pressure at the top of the first fractionation unit.

Preferably, in (d), the number of theoretical trays of the second fractionation unit is in the range of from 1 to 100, preferably from 3 to 50 more preferably from 5 to 30.

According to a preferred embodiment of the present invention, the second fractionation unit in (d) is operated with reflux. While it is generally possible to use any suitable stream as reflux, it is preferred to use a portion of S4c, preferably after condensation, as reflux. Preferably, the reflux ratio is in the range of from 0.5:1 to 1:1, more preferably from 0.7:1 to 1:1, more preferably from 0.9:1 to 1:1. The term "reflux ratio" as used in this context is defined as the ratio of the reflux flow relative to S4c and is a measure of how much of the material going up the top of the second fractionation unit is returned back to the second fractionation unit as reflux.

According to a conceivable embodiment of the present invention, the second fractionation unit in (d) is operated without reflux. According to this embodiment, it is preferred to feed the at least part of the stream S4a to the top of the second fractionation unit. In this case, it is generally possible to operate the second fractionation unit as a reboiled stripping unit or as a non-reboiled stripping unit. If the second fractionation unit is designed as a reboiled stripping unit, it is preferred that at least one heat exchanger is suitably arranged at the bottoms of the second fractionation unit in order to allow for the evaporation of the bottoms stream of the second fractionation unit wherein the stripping vapor is generated internally. If the second fractionation unit is designed as a non-reboiled stripping unit, it is preferred that at least one external vapor feed stream is employed as stripping vapor and to omit the at least one heat exchanger arranged at the bottoms of the second fractionation unit. Generally, it is possible to combine at least one heat exchanger arranged at the bottoms of the second fractionation unit and at least one external vapor feed stream. Preferably, in case the second fractionation unit is operated with reflux, the second fractionation unit is operated as a non-reboiled stripping unit.

Therefore, the present invention relates to the process as described above, wherein in (d), the first fractionation unit is operated without reflux, the at least part of the vapor fraction stream S4a subjected to the vapor-liquid fractionation in the second fractionation unit preferably not being condensed prior to subjecting to the vapor-liquid fractionation in the second fractionation unit, and the second fractionation unit is operated with reflux, wherein a fraction of the vapor fraction stream S4c is used, after condensation, as reflux and wherein the reflux ratio is preferably in the range of from 0.5:1 to 1:1, more preferably from 0.7:1 to 1:1, more preferably from 0.9:1 to 1:1.

According to the present invention, it is preferred that from 90 to 99.99 weight-%, more preferably from 95 to 99.9 weight-%, more preferably from 98 to 99.9 weight-% of S4 consist of acetonitrile and water, and that from 0.0001 to 0.2 weight-%, preferably from 0.001 to 0.15 weight-%, more preferably from 0.005 to 0.1 weight-% of S4 consist of the at least one component B.

Step (e)

According to step (e) of the process of the present invention, at least a portion of S4 and at least a portion of S2 are recycled to step (a) of the process of the present invention. Generally, it is possible to recycle S4 or the portion thereof without any further work-up stages to step (a). Preferably, S4 or the portion thereof is subjected to a downstream work-up stage prior to recycling to (a). —Further, according to step (e) of the process of the present invention, at least a portion of S2 is recycled to step (a) of the process of the present invention. Generally it is possible to recycle S2 or the portion thereof without any further work-up stages to step (a). Preferably, S2 or the portion thereof is subjected to a downstream work-up stage prior to recycling to (a). In case S2 or the portion thereof is subjected to a downstream work-up stage prior to recycling to (a), and in case during this work-up stage, the weight ratio of acetonitrile relative to the at least one component B is increased compared to the respective weight ratio of S2, said weight ratio after the work-up stage is lower than the respective weight ratio of S4.

Therefore, the present invention relates to the process as described above, wherein (e) comprises recycling at least a portion of S4, optionally after work-up, to (a), and recycling at least a portion of S2, optionally after work-up, to (a).

Preferably, in the work-up stage regarding S4, S4 or the portion thereof is combined with at least a portion of S2. Preferably, in the work-up stage regarding S2, S2 or the portion thereof is combined with at least a portion of S4. The respectively obtained combined stream is recycled, optionally after work-up, to (a). More preferably, the complete stream S4, optionally after having separated a portion thereof used as reflux to the fractionation unit employed in (d), and the complete stream S2 are suitably combined and the combined stream is recycled, optionally after work-up, to (a). More preferably, S4 or the portion thereof is condensed and combined with the stream S2 obtaining a liquid stream. Preferably, the complete stream S4, optionally after having separated a portion thereof used as reflux to the fractionation unit employed in (d), is condensed and combined with S2 obtaining a liquid stream. Preferably, this liquid stream is subjected to a downstream work-up stage prior to recycling to (a).

Therefore, the present invention relates to the process as described above, wherein (e) comprises combining at least a portion of S4 and at least a portion of S2, and recycling the combined stream, optionally after work-up, to (a).

According to the present invention, said downstream work-up stage regarding the combined stream preferably comprises an acetonitrile-water separation from which separation a stream enriched in acetonitrile is obtained which, optionally after further work-up, is preferably recycled to (a).

Therefore, the present invention relates to the process as described above, wherein (e) comprises combining at least a portion of S4 and at least a portion of S2, subjecting the combined stream to an acetonitrile-water separation obtaining a stream enriched in acetonitrile, and recycling the stream enriched in acetonitrile, optionally after further work-up, to (a).

Therefore, the present invention also relates to the process as described above, wherein (e) comprises working-up S4, said working-up comprising combining at least a portion of S4, preferably after condensation, with S2 obtaining a preferably liquid stream, subjecting said preferably liquid stream to acetonitrile-water separation obtaining a stream enriched in acetonitrile, and recycling said stream enriched in acetonitrile, optionally after further work-up, to (a).

Regarding said acetonitrile-water separation, no specific restrictions exist. Preferably, the acetonitrile-water separation comprises adding a stream P preferably comprising at least 95 weight-%, based on the total weight of P, of C3 wherein C3 is propene optionally admixed with propane, preferably a liquid stream P,
either to S2, wherein the resulting stream is combined with at least the portion of S4 to obtain a preferably liquid stream S5;
or to at least the portion of S4, wherein the resulting stream is combined with S2 to obtain a preferably liquid stream S5;
or, preferably, to a liquid stream obtained from combining at least the portion of S2 and at least the portion of S4.

It is also possible to add a first portion of the stream P to at least the portion of S4 and to add a second portion of the stream P to S2 and to combine the two resulting stream to obtain a preferably liquid stream S5. The preferably liquid stream P preferably comprises at least 95 weight-%, based on the total weight of P, of C3 wherein C3 is propene optionally admixed with propane. Regarding C3, it is preferred that the minimum weight ratio of propene relative to propane of 7:3. In the context of the present invention, all embodiments regarding the addition of the stream P described above are encompassed by the term "subjecting the combined stream to an acetonitrile-water separation obtaining a stream enriched in acetonitrile" as used in the context of step (e) above.

Preferably, at least 95 weight-% of P consist of propene or a mixture of propene with propane. If P contains a mixture of propene and propane, the weight ratio of propene relative to propane will be at least 7:3. Therefore, propene streams can be employed as P or C3 which have varying contents of propane. For example, commercially available propene can be employed as P or C3 which may be either a polymer grade propene or a chemical grade propene. Typically, polymer grade propene will have a propene content of from 99 to 99.8 weight-% and a propane content of from 0.2 to 1 weight-%. Chemical grade propene will typically have a propene content of from 92 to 98 weight-% and a propane content of from 2 to 8 weight-%. According to a preferred embodiment of the present invention, a stream P is employed, at least 95 weight-% thereof consisting of C3, wherein C3 is a mixture of propene and propane and the content of C3 regarding propene is in the range of from 92 to 98 weight-%, preferably from 94 to 97 weight-%, and the content of C3 regarding propane is in the range of from 2 to 8 weight-%, preferably from 3 to 6 weight-%.

As far as the amount of P is concerned, it is preferred that P is added so that in S5, the weight ratio of C3 relative to acetonitrile is in the range of from 0.2:1 to 5:1, preferably from 0.5 to 1 to 2:1. Therefore, preferably from 90 to 99.9 weight-%, more preferably from 95 to 99.8 weight-%, more preferably from 98 to 99.5 weight-% of the stream S5 consist of acetonitrile, water and C3, and preferably from 0.01 to 3 weight-%, preferably from 0.015 to 2.5 weight-%, more preferably from 0.02 to 1.5 weight-% of the stream S5 consist of the at least one component B, wherein the weight ratio of acetonitrile relative to water is preferably greater than 1:1 and wherein weight ratio of C3 relative to acetonitrile is preferably in the range of from 0.2:1 to 5:1, more preferably from 0.5 to 1 to 2:1, wherein regarding C3, the weight ratio of propene relative to propane is at least 7:3.

Preferably, the stream S5 is subjected to a suitably temperature and a suitable pressure by which temperature and pressure treatment two liquid phases L1 and L2 are formed. It was found that it is beneficial for the breakup into these phases L1 and L2 to subject the stream S5 to as low a temperature as possible with the proviso that the temperature is still suitable; for example, the temperature shall not be so low that a solid phase such as ice is formed.

Preferably, the liquid phase L1 enriched in acetonitrile is suitably separated from L2 and recycled to (a), optionally after further work-up. Concerning the temperature and pressure treatment, no specific restrictions exits, provided that the two phases L1 and L2 are formed wherein L1 is enriched in acetonitrile. Preferably, S5 is brought to a temperature of 92° C. at most. According to the present invention, it is preferred to bring S5 to a temperature in the range of from 5 to 90° C., preferably from 7- to 80° C., more preferably from 8 to 60° C., more preferably from 9 to 40° C., and more preferably from 10 to 30° C. Preferably, S5 is subjected to a pressure of at least 10 bar so that S5 will be present essentially or completely in its liquid form. The term "essentially in its liquid form" as used in this context of the present invention relates to an embodiment according to which at least 95 weight-%, more preferably at least 99 weight-% and more preferably at least 99.9 weight-% of S5 are present in liquid form after being subjected to above-mentioned temperatures and pressures. According to the present invention, it is preferred to subject S5 to a pressure of at least 15 bar, more preferably to a pressure in the range of from 15 to 50 bar, more preferably from 15 to 40 bar, more preferably from 15 to 30 bar, and more preferably from 15 to 25 bar.

Bringing S5 to above-mentioned temperature can be accomplished by any suitable method. According to the present invention, it is preferred to use one or more suitable heat transfer media, e.g. water, in a suitable apparatus, e.g. a shell and tube heat exchanger. Subjecting S5 to above-mentioned pressure can be accomplished by any suitable method. According to the present invention, it is preferred to use a suitable pump such as a centrifugal pump or a radial pump.

Preferably, at least 95 weight-%, preferably at least 98 weight-% of L1 consist of C3, acetonitrile, water and the at least one component B, wherein the water content of L1 is less than 10 weight-%, preferably in the range of from 1 to 5 weight-%, based on the total weight of L1.

Preferably, at least 98 weight-% of L2 consist of C3, acetonitrile, water and the at least one component B, wherein the C3 content of L2 is 5 weight-% at most, based on the total weight of L2, and the acetonitrile content of L2 is less than 45 weight-%, preferably in the range of from 10 to 35 weight-%, based on the total weight of L2.

According to the present invention, temperatures and pressures as described above allow for the existence of two distinct liquid phases L1 and L2. Preferably, the two distinct liquid phases L1 and L2 are suitably separated from each other. Generally, for this separation of the two liquid phases, every conceivable method can be applied. Possible apparatuses used for the separation of L1 from L2 are, for example, gravity settlers, settlers with coalescing aids such as weirs, inclined plates separator, coalescers such as, for example, mats, beds, layers of porous or fibrous solids, or membranes, stagewise mixer-settler equipment, hydrocyclones, centrifuges, suitable columns with or without energy input. Generally, batch mode or continuous mode is conceivable. Preferably, a gravity settler such as vertical or horizontal gravity settler is employed. Still more preferably, a horizontal gravity settler is employed. It was found that due to the considerable density difference and low viscosities achieved for the liquid phases L1 and L2 according to the inventive method, the gravity settler, one of the simplest apparatus, may be employed. According to the present invention, it is conceivable that at least one liquid phase separation improving agent such as at least one suitable anti-emulsifying, demulsifying or emulsion breaking agent is added. Generally, it is possible to add said liquid phase separation improving agent to S4 or to S5 or to S4 and S5. The amount of liquid phase separation improving agent added is preferably at most 1 weight-% based on the total weight of S4 and/or S5. Typically, the amount will be less than 1 weight-%% such as below 0.5 weight-% or below 0.1 weight-%. Suitable agents are known by the skilled person. Reference is made, e.g., to K. J. Lissant, Making and Breaking Emulsions, Res. Lab., Petrolite Corp., St. Louis, Mo., USA, in: K. J. Lissant (ed.), Emulsion Technology (1974), chapter 2, pp 111-124, Dekker, N.Y.; and to S. E. Taylor, Chem. Ind. (1992), pp 770-773.

Therefore, step (e) of the process of the present invention preferably comprises
  (i) preparing a preferably liquid stream S5 by adding a preferably liquid stream P to S2, or to at least the portion of S4, or to the liquid stream obtained from combining S2 and at least the portion of S4,
    wherein P comprises at least 95 weight-% of C3, based on the total weight of P, wherein C3 is propene optionally admixed with propane with a minimum weight ratio of propene relative to propane of 7:3, and wherein P is preferably added in an amount so that in S5, the weight ratio of C3 relative to acetonitrile is in the range of from 0.2:1 to 5:1, preferably from 0.5:1 to 2:1;

(ii) subjecting S5 to a temperature of 92° C. at most and a pressure of at least 10 bar, preferably to a temperature in the range of from 5 to 90° C. and a pressure in the range of from 15 to 50 bar, more preferably to a temperature in the range of from 25 to 45° C. and a pressure in the range of from 15 to 25 bar, obtaining a first liquid phase L1 and a second liquid phase L2, wherein at least 95 weight-%, preferably at least 98 weight-% of L1 consist of C3, acetonitrile, water and the at least one component B, the water content of L1 being less than 10 weight-%, preferably in the range of from 1 to 5 weight-%, based on the total weight of L1, and wherein at least 95 weight-%, preferably at least 98 weight-% of L2 consist of C3, acetonitrile, water and the at least one component B, the C3 content of L2 being 5 weight-% at most, based on the total weight of L2, and the acetonitrile content of L2 being less than 45 weight-%, preferably in the range of from 10 to 35 weight-%, based on the total weight of L2;

(iii) separating L1 from L2, preferably in a gravity settler;
(iv) recycling L1 as the stream enriched in acetonitrile, optionally after further work-up, to (a).

The Stream L2

Preferably, from the process of the present invention, a liquid phase L2 is obtained which essentially consists of water and acetonitrile wherein the weight ratio of acetonitrile:water in L2 is less than 1. The term "essentially consists of acetonitrile and water" as used in this context of the present invention refers to a liquid phase L2 wherein at least 90 weight-% of L2 consist of acetonitrile and water. Preferably, at least 95 weight-%, more preferably at least 97 weight-% and still more preferably at least 98 weight-% of L2 consist of the C3, acetonitrile, and water, wherein the C3 content of L2 is 5 weight-% at most, preferably 3 weight-% at most, and more preferably 2 weight-% at most based on the total weight of L2. As far as the acetonitrile is concerned, the respective content of L2 is preferably less than 45 weight-%, more preferably in the range of from 10 to 40 weight-%, more preferably from 10 to 35 weight-%, based on the total weight of L2.

Generally, the liquid phase L2 can be used in any suitable process. For example, it is conceivable that the liquid phase L2 is employed as a stream which is passed to an oxidation reaction or a work-up stage downstream of said oxidation reaction wherein acetonitrile is used as solvent and wherein propene is oxidized, such as an epoxidation reaction wherein acetonitrile is used as solvent and wherein propene is oxidized by hydrogen peroxide to obtain propylene oxide.

Preferably, the liquid phase L2, prior to being employed in a suitable process, is subjected to at least one further separation stage. A preferred method for said separation comprises subjecting the liquid phase L2 to a distillation stage. Preferably, distillation is carried out in a suitable manner so that a stream TL2 is obtained which contains from 75 to 95 weight-%, preferably from 80 to 85 weight-% acetonitrile, based on the total weight of TL2. Generally, distillation of L2 can be carried out in one, two, or more distillation towers. If this distillation is carried out in one distillation tower, the dew-point at the top of said distillation tower is typically at least 40° C., preferably in the range of from 40 to 80° C., more preferably in the range of from 40 to 65° C. Typically, the number of theoretical trays is in the range of from 10 to 25. Typical reflux ratios are in the range of from 0.5 to 3. By such process, stream TL2 is obtained as top stream from the distillation tower. The respective bottoms stream, BL2, is preferably essentially free of acetonitrile. In this context, the term "essentially free of acetonitrile" refers to an embodiment according to which the acetonitrile content of BL2 is 500 weight-ppm at most, preferably 300 weight-ppm at most, more preferably 100 weight-ppm at most, based on the total weight of BL2.

Surprisingly, it was found that it is possible to subject liquid phase L2 to an especially designed distillation stage which allows for a highly heat-integrated distillation process. Thus, it was found that separation of L2 is advantageously carried out using a two pressure distillation process, wherein in a first distillation tower, distillation is carried out at a top pressure which is higher than the top pressure of a second distillation tower coupled with said first distillation tower, wherein the condenser used to condense the top stream of the first distillation tower is used simultaneously as the vaporizer of the second distillation tower. According to this preferred embodiment, liquid stream L2 is preferably introduced in said first distillation tower from which a first bottoms stream and a first top stream are obtained. Preferably, said first distillation tower is operated at conditions which allow for obtaining a vapor top stream VTL2 which contains of from 50 to 70 weight-%, preferably from 55 to 65 weight-% of acetonitrile, based on the total weight of VTL2. Typically, said first distillation tower is operated at pressures at the top of the tower in the range of from 10 to 20 bar, preferably from 10 to 15 bar. Generally, the first distillation tower has from 10 to 25, preferably from 15 to 20 theoretical trays. Generally, the reflux ratio of said first distillation tower is in the range of from 0.25:1 to 2:1, preferably of from 0.25:1 to 1:1. The respective bottoms stream obtained from the first distillation tower is preferably essentially free of acetonitrile. In this context, the term "essentially free of acetonitrile" refers to an embodiment according to which the acetonitrile content of the bottoms stream of the first distillation tower is 500 weight-ppm at most, preferably 300 weight-ppm at most, more preferably 100 weight-ppm at most, based on the total weight of the bottoms stream of the first distillation tower. In the following, said bottoms stream obtained from said first distillation tower, optionally admixed with the bottoms stream obtained from the second distillation tower as described hereinunder, is referred to as stream BL2. In the two-pressure distillation process, at least a portion of, preferably all of VTL2 is suitably condensed, and this condensed stream is introduced into the second distillation tower from which a second bottoms stream and a second top stream are obtained. Preferably, said second distillation tower is operated at conditions which allow for obtaining a top stream TL2 which contains of from 75 to 95 weight-%, preferably from 80 to 85 weight-% of acetonitrile, based on the total weight of TL2. Typically, said second distillation tower is operated at pressures at the top of the tower in the range of from 1 to 5 bar, preferably from 1 to 2 bar. Generally, the second distillation tower has from 8 to 20, preferably from 10 to 15 theoretical trays. Generally, the reflux ratio of said second distillation tower is in the range of from 0.5 to 5, preferably of from 1 to 3. The respective bottoms stream obtained from the second distillation tower is preferably essentially free of acetonitrile. In this context, the term "essentially free of acetonitrile" refers to an embodiment according to which the acetonitrile content of the bottoms stream of the second distillation tower is 500 weight-ppm at most, preferably 300 weight-ppm at most, more preferably 100 weight-ppm at most, based on the total weight of the bottoms stream of the second distillation tower.

Preferably, TL2 obtained from the respective distillation tower is at least partially, preferably completely recycled into the inventive process. More preferably, TL2 is either combined with S4 and/or with S5 and/or with P, and optionally also combined with TL1 as described hereinunder.

If the stream S5 contains at least one propylene glycol, the stream BL2 obtained from said distillation preferably contains the at least one propylene glycol in an amount of from 1 to 5 weight-%, more preferably in an amount of from 2 to 5 weight-%, based on the total weight of BL2, whereas stream TL2 is essentially free of the at least one propylene glycol. In this context of the present invention, the term "TL2 is essentially free of the at least one propylene glycol" refers to an embodiment according to which the content of TL2 as to the at least one propylene glycol is 500 weight-ppm at most TL2 is essentially free of the at least one propylene glycol, preferably 200 weight-ppm at most. If BL2 contains no or essentially no propylene glycol, it is preferred to pass BL2 directly to a suitable waste water treatment plant such as a biological waste water treatment plant. It was found that no specific treatment for the waste water produced by the inventive process is required, rendering the process even more cost-efficient and environment-friendly. If BL2 contains at least one propylene glycol in significant amounts, such as in an amount of from 1 to 5 weight-%, more preferably in an amount of from 2 to 5 weight-%, based on the total weight of BL2, it can be preferred to pass BL2 to a suitable propylene glycol separation stage wherein the at least one propylene glycol is suitably separated from water and/or wherein two or more different propylene glycols are separate from each other. This process for the separation of the at least one propylene glycol from BL2 can be carried out, for example, by evaporating the mixture in at least two, preferably three evaporation and/or distillation stages, preferably three evaporation stages, at decreasing operating pressures, preferably in the ranges of 1.5 to 5.5 bar at a temperature of 111 to 155° C., followed by 1.3 to 5.0 bar at a temperature of 107 to 152° C., followed in turn by 0.7 to 4.0 bar at a temperature of 90 to 144° C., thus obtaining mixture BL2-a and mixture BL2'-b; and separating the mixture BL2-a in at least one further distillation step, obtaining a mixture BL2-I comprising at least 70 weight-% of water and a mixture BL2-II comprising less than 30 weight-% of water. It is especially preferred to further separate mixture BL2-b into a mixture BL2-Ia comprising at least 90 weight-% of water and a mixture BL2-Ib comprising less than 95 weight-% of water by means of reverse osmosis. Preferably, the at least one propylene glycol is separated from the mixture BL2-II, preferably admixed with mixture BL2-Ib, in at least one further distillation step. More preferably, mixtures BL2'-b and BL2-I are combined and further separated into mixture BL2-Ia comprising at least 90 weight-% of water and mixture BL2-Ib comprising less than 95 weight-% of water by means of reverse osmosis.

Therefore, the present invention also relates to a method as described above wherein (aa) L2 is introduced into the first distillation tower from which a vapor top stream VTL2 is obtained containing from 50 to 70 weight-% acetonitrile, based on the total weight of top stream VTL2, the distillation preferably being carried out at a top pressure of from 10 to 20 bar; and (bb) at least partially condensing VTL2 obtained in (aa) and introducing the condensed stream into the second distillation tower wherefrom TL2 is obtained as top stream, the distillation preferably being carried out at a top pressure of from 1 to 5 bar, wherein preferably, the condenser used to condense VTL2 is simultaneously used as vaporizer of the second distillation tower.

The Stream L1

According to the present invention, it is preferred that the stream L1 separated according to (iii) is recycled to (a) after further work-up.

Preferably, this further work-up serves for separating C3, preferably a portion of C3, from the acetonitrile. A conceivable method is, for example, evaporation of the liquid phase L1 by decompression at a suitable pressure. Preferably, the temperature of the liquid phase is kept essentially constant during decompression. By this decompression, C3 is obtained in gaseous form. Thereafter, it is possible to recycle at least a portion of this gaseous C3 stream, after suitable compression to obtain a liquid stream, for example as at least a portion of stream P.

Preferably, L1 is subjected to fractionation, more preferably to distillation, from which a stream is obtained which is enriched in acetonitrile and which is preferably recycled to (a), optionally after a work-up. Preferably, said stream enriched in acetonitrile is recycled to (a) without further workup. More preferably, this distillation is carried out in a suitable manner so that a stream TL1 is obtained which contains at least 90 weight-%, preferably at least 95 weight-% C3, based on the total weight of TL1. Preferably according to this distillation, a stream BL1 is obtained of which preferably at least 95 weight-%, more preferably at least 98 weight-% consist of C3, acetonitrile, water and the at least one component B. More preferably, the C3 content of BL1 is in the range of from 7 to 18 weight-%, preferably from 10 to 15 weight-%, in each case based on the total weight of BL1.

Generally, this distillation of L1 can be carried out according to any suitable method. For example, one, two or more distillation towers can be employed provided that above-mentioned streams TL1 and BL1 are obtained. Preferably, in said distillation stage, one distillation tower is employed. More preferably, said distillation is carried out at a dew-point at the top of said distillation tower of at least 40° C., preferably in the range of from 40 to 80° C., more preferably in the range of from 40 to 70° C. Preferably, the number of theoretical trays is in the range of from 10 to 20. Preferred reflux ratios are in the range of from 0.01:1 to 0.2:1 such as from 0.05:1 to 0.15:1.

Therefore, the present invention also relates to the process as described above, further comprising working up L1, said working-up comprising subjecting L1 to a distillation stage wherefrom a bottoms stream BL1 is obtained, wherein at least 95 weight-%, preferably at least 98 weight-% of BL1 consist of C3, acetonitrile, water and the at least one component B, wherein the C3 content of BL1 is in the range of from 7 to 18 weight-%, preferably from 10 to 15 weight-%, and recycling BL1 as the stream enriched in acetonitrile, optionally after no further work-up, to (a). Preferably, from 0.01 to 5 weight-%, more preferably from 0.015 to 3 weight-%, more preferably from 0.02 to 2 weight-% of BL1 consist of the at least one component B. In particular, the distillation tower is operated in a suitable manner, for example by adjusting the energy input in the sump, which leads to a stream BL1 having a propene content which, when being fed back to the epoxidation reaction as recycling stream, results in a molar ratio of propene relative to hydrogen peroxide in stream (1) in the range of from 0.9:1 to 3.0:1, more preferably from 0.98:1 to 1.6:1, more preferably from 1.0:1 to 1.5:1 such as from 1.2:1 to 1.4:1.

Thus, the present invention relates to the process as described above, which process comprises working-up L1 comprising subjecting L1 to a distillation stage wherefrom a bottoms stream BL1 is obtained, wherein at least 95 weight-%, preferably at least 98 weight-% of BL1 consist of C3, acetonitrile, water and the at least one component B, wherein the C3 content of BL1 is in the range of from 7 to 18 weight-%, preferably from 10 to 15 weight-%, and recycling BL1 as the stream enriched in acetonitrile, preferably without any further work-up, to (a).

Preferably from 0.01 to 5 weight-%, more preferably from 0.015 to 3 weight-%, more preferably from 0.02 to 2 weight-% of BL1 consist of the at least one component B.

Further it was found that combining the inventive separation of L1 from L2 and the downstream separation of TL1 from BL1 allows for a highly integrated design of the process of the present invention. On the one hand, stream TL1 is especially suitable for being recycled into the inventive process as at least a portion of P. If, in addition to at least a portion of TL1, further C3 is added to S1, this further source of C3 may be suitably chosen. For example, additional C3 can be added as fresh propene, for example as chemical grade propene containing about 95 weight-% propene and about 5 weight-% propane. All other suitable sources of additional C3 are conceivable, such as a C3 stream obtained from a supplier in a Verbund site or the like. Further, it was found that the more C3 is recycled via TL1, the more effective the phase separation according to (i) to (iii) of the inventive process works in terms of as complete a separation of S1 as possible. Therefore, it is preferred that at least a portion of TL1, preferably all of TL1 is recycled into (ii).

Generally, it is conceivable that the part-steam distillation may be arranged at another position in the epoxidation downstream process, preferably at a location with access to the acetonitrile solvent stream.

Preferably, such a conceivable location would be a location where the acetonitrile solvent stream is free of or essentially free of propene and optionally propane, and/or where the acetonitrile solvent stream is free of or essentially free of hydrogen peroxide. More preferably, such a conceivable location would be a location downstream the epoxidation reaction step (a) and upstream the location at which the stream P is admixed, upstream the liquid-liquid separation in (ii). More preferably, such a conceivable location would be a location downstream the location where propylene oxide is removed from the acetonitrile solvent stream in step (b) and upstream the location at which the stream P is admixed, upstream the liquid-liquid separation in (ii). Most preferably, the location of the part-stream distillation is the location as described above where S3 as a portion of the stream S1 is subjected to distillation. Further, it is generally conceivable that at more than one location in the epoxidation downstream process, a part-stream distillation according to which a portion, preferably a minor portion of the acetonitrile solvent stream is subjected to distillation, is arranged.

The present invention is illustrated by the following examples and comparative examples.

EXAMPLES

Example 1: A Preferred Process According to the Invention—General Setup

As to the abbreviations, reference is made to the scheme according to FIGS. 1 and 3, generally described in the section "Description of the Figures" hereinbelow. All pressures given are absolute pressures.

1.1 Preparation of Stream S0 (Step (a))

a) Epoxidation in an Epoxidation Main Reactor (Epoxidation Unit A)

The main reactor A was a vertically mounted tube-bundle reactor with 5 tubes (length of the tubes: 12 m, internal tube diameter: 38 mm), each tube being equipped with an axially placed multi-point thermocouple with 10 equally spaced measuring points encased in a suitable thermowell with a diameter of 18 mm. Each tube was charged with 17.5 kg of the ZnTiMWW catalyst moldings as prepared according to Reference Example 1, section 1.8 (post-treated moldings). Free space eventually remaining was filled with steatite spheres (diameter of 3 mm). The heat of reaction was removed by circulating a thermostatized heat transfer medium (water/glycol mixture) on the shell side in co-current to the feed. The flow rate of the heat transfer medium was adjusted so that the temperature difference between entrance and exit did not exceed 1° C. The reaction temperature referred to hereinbelow was defined as the temperature of the heat transfer medium entering the reactor shell. At the reactor exit, the pressure was controlled by a pressure regulator and kept constant at 20 bar.

The reactor was fed from below with a liquid monophasic stream (1). Stream 1 was prepared by mixing four streams (2), (3), (3a) and (4). The temperature of stream (1) was not actively controlled, but was usually in the range from 20 to 40° C.:

Stream (2) having a flow rate of 85 kg/h. At least 99.5 weight-% of stream (2) consisted of acetonitrile, propene and water. This stream (2) came from the bottoms of the acetonitrile recycle distillation unit (J).

Stream (3) having a flow rate of 15 kg/h was an aqueous hydrogen peroxide solution having a hydrogen peroxide concentration of 40 weight-% ("crude/washed" grade from Solvay with a TOC in the range of 100 to 400 mg/kg. The aqueous hydrogen peroxide solution was supplied from a storage tank, allowing for a continuous feeding, and fed using a suitable metering pump.

Stream (3a) was an aqueous stream comprising dissolved potassium formate. The further stream was supplied from a storage tank, allowing for a continuous feeding, and was fed using a suitable metering pump. The concentration of the potassium formate was 2.5 weight-%, the feed rate of the stream (S3a) was 370 g/h. Stream (3a) was thoroughly mixed with stream (3) before the combined stream was mixed with the stream resulting from mixing stream (2) and (4).

Stream (4) was a make-up stream of pure acetonitrile (chemical grade, from Ineos, purity about 99.9%, containing between 70-180 weight-ppm propionitrile, 5-20 weight-ppm acetamide and less than 100 weight-ppm water as impurities). Enough fresh acetonitrile was added to compensate for losses in the process. Under regular conditions, an average of from 100 to 150 g/h of make-up acetonitrile were added.

The output stream leaving the epoxidation unit A was sampled every 20 minutes in order to determine the hydrogen peroxide concentration using the titanyl sulfate method and to calculate the hydrogen peroxide conversion. The hydrogen peroxide conversion was defined as $100\times(1-m_{out}/m_{in})$ wherein $m_{in}$ is the molar flow rate of $H_2O_2$ in the reactor feed and $m_{out}$ is the molar flow rate of $H_2O_2$ in the reactor outlet. Based on the respectively obtained hydrogen peroxide conversion values, the inlet temperature of the heat transfer medium was adjusted in order to keep the hydrogen peroxide conversion essentially constant in the range of from 90 to 92%. The inlet temperature of the heat transfer medium was set at 30° C. at the start of a given run with a fresh batch of the epoxidation catalyst and was increased, if necessary, to maintain the hydrogen peroxide conversion in the mentioned range. The required temperature increase was usually less than 1 K/d.

b) Intermediate Removal of Propylene Oxide (Distillation Unit B)

After pressure release, the effluent from the epoxidation unit A (stream (5)) was sent to an intermediate propylene oxide removing column (distillation unit B) operated at about 1.1 bar. The column was 6 m high, had a diameter of 200 mm and was equipped with 30 bubble trays, an evaporator, and a condenser. The feed to the column entered above bubble tray 25 (counted from the top). The overhead stream leaving the column with about 50° C. mainly contained propylene oxide, unconverted propene and small amounts of oxygen formed as byproduct. This stream was partly condensed (T=15-25° C.), and the condensed liquid served as an internal reflux stream whereas the gaseous part (stream (6)) was sent to the lights separation column (distillation unit D).

The bottoms temperature of the intermediate propylene oxide removal column was about 80° C. The bottoms stream (stream (7)) was almost free of propylene oxide (<300 wt.-ppm) and was a mixture of acetonitrile (about 78-80 weight-%), water (about 18-20 weight-%), unconverted hydrogen epoxide and heavy boilers having a normal boiling point of above 100° C., the main heavy boiler being propene glycol. This bottoms stream (7) was subsequently cooled to 35° C. and pumped pump to the finishing reactor (epoxidation unit C; see section c) below) using a suitable metering pump.

c) Epoxidation in a Finishing Reactor (Epoxidation Unit C)

The total feed stream to the finishing reactor C was obtained by mixing stream (7) obtained according to section b) above with a stream (8) of polymer grade liquid propene containing propane (purity about ≥99.5%, feed rate: 0.9 kg/h, at ambient temperature). Both streams (7) and (8) were mixed using a static mixer and fed to the bottom of the finishing reactor C.

The finishing reactor C was a fixed bed reactor operated adiabatically. In this context, the term "adiabatic" refers to an operation mode according to which no active cooling is carried out and according to which the finishing reactor is suitably insulated in order to minimize heat losses). The finishing reactor C had a length of 4 m and a diameter of 100 mm. The reactor was filled with 9 kg of the same epoxidation catalyst which was used in the main epoxidation reactor A. Spare space was filled with steatite spheres (diameter of 3 mm). The operating pressure of the finishing reactor C was 10 bar which was kept constant by a suitable pressure regulator at the reactor exit. The output of the finishing reactor C was sampled every 20 min in order to determine the hydrogen peroxide concentration using the titanyl sulfate method.

The effluent of the finishing reactor C, stream (9), was depressurized into a flash drum, and both the liquid and the gas from this drum were fed to a light boiler separation column (distillation unit D).

The stream (6) obtained from the top of the intermediate propylene oxide removing column (distillation unit B) and the stream (9) obtained as effluent from the finishing reactor C (epoxidation unit C) together constitute the stream S0 according to the present invention.

This stream S0 had in average an acetonitrile content of from 69 to 70 weight-%, a propylene oxide content of 9.8 weight-%, a water content of 17 weight-%, a propene content of about 3 weight-%, a propane content of about 0.05 weight-%, a hydrogen peroxide content of about 250 weight-ppm, a propene glycol content of about 0.1 weight-% and an oxygen content of about 150 weight-ppm.

1.2 Separation of Propylene Oxide from Stream S0 to Obtain Stream S1 (Step (b))

a) Separation of Light Boilers from Streams (6) and (9) (Stream S0) to Obtain a Stream (11) (Stream S01 According to Step (I) of the Present Invention)

The top stream from the intermediate propylene oxide removing column (distillation unit B) (stream (6), see section 1.1 b) above) and the depressurized outlet stream of the finishing reactor C (stream (9), see section 1.1 c) above) were sent to a light boiler separation column (distillation unit D) operated at 1.1 bar. The distillation column had a length of 8.5 m, a diameter of 170 mm, and was equipped with 40 bubble trays, an evaporator at the bottom and a condenser at the top. The column was operated as a mixed washing/distillation tower. As a washing agent, part of the bottoms stream of distillation unit E (stream 14, about 20-30 kg/h) was taken off, cooled to 10° C. and introduced at the top of the column. Liquid and gaseous inlet streams were introduced the column at different points. The feed point of the liquid stream (stream (6) plus the liquid portion of stream (9)) was above bubble tray 37; the gaseous stream was introduced into the column above bubble tray 28 (counted from the top).

The gaseous stream (10) leaving the cooling means at the top of the column contained mainly propene, propane (which was contained as impurity in the polymer-grade propene used), oxygen formed as a by-product and small amounts of other light boilers (acetonitrile (about 4.7 volume-%), propionaldehyde (about 200 volume-ppm), acetone (about 100 volume-ppm), $H_2$ (about 400 volume-ppm), $CO_2$ (about 400 volume-ppm) and acetaldehyde (about 100 volume-ppm)), and was essentially free of propylene oxide (less than 300 volume-ppm). This top stream was sent to the flare for disposal.

The bottom stream of the light boiler separation column (stream (11), that is stream S01 of the present invention) having a temperature of 70° C., had a propene content of from 100 to 200 weight-ppm.

b) Separation of Propylene Oxide from Stream (11) (Stream S01) to Obtain a Stream S02 according to Step (II) of the Present Invention The stream S01 obtained according to section 1.2 a) above was introduced into a distillation column (distillation unit E) in order to separate propylene oxide from the stream S01. The column had a height of 50 m and a diameter of 220 mm and was equipped with a packing (Sulzer BX64) with a total packing length of 27.5 m divided into 8 beds with a length of 3060 mm each and two beds with a length of 1530 mm each. Between each bed intermediate flow distributors were installed. The column was operated at a top pressure of 750 mbar. The feed point of stream S01 was located below the fourth packing bed, counted from the top.

The overhead stream of the column was condensed and partly returned to the column as reflux (reflux ratio approximately 5:1). The remainder (stream (12)), having a flow rate of 10.1 kg/h, was taken as overhead product and essentially consisted of propylene oxide having a purity of more than 99.9 weight-%.

The bottoms evaporator was operated in such a way that the propylene oxide concentration in the bottoms stream was below 100 weight-ppm. The resulting temperature of the bottoms stream was about 69° C. The stream S02 was then divided in two. The major portion of it (stream (13), with a flow rate of ca. 85 kg/h) was sent to the next distillation column (distillation unit F). The remainder (stream (14), 20-30 kg/h) was cooled and recirculated to the top of the light boiler separation column (distillation unit D) as washing agent as described above in section 1.2 a).

This stream S02 had an acetonitrile content of about 80 weight-%, a propylene oxide content of less than 100 wt.-ppm, a water content of about 20 weight-%, a propene glycol content of about 0.1 weight-% and a hydroxypropanol content of about 0.1 weight-%.

c) Separation of Light Boiling Compounds from Stream (13) (Stream S02) to Obtain a Stream (16) (Stream S1 according to Step (IIIb) of the Present Invention)

The stream S02 obtained according to section 1.2 b) above was introduced into a lights separation column (distillation unit F). This lights separation column had a height of 8 m and a nominal diameter of 150 mm and was equipped with 35 bubble trays. The column was operated at a top pressure of 2 bar, and the stream S02 was introduced above bubble tray number 7 (counted from the bottom).

The overhead stream obtained (stream (15), flow rate about 1 kg/h) left the column with a temperature of from 40 to 45° C. and was not condensed as the column was operated with no internal reflux stream. Besides acetonitrile (6500 vol.-ppm), this overhead stream contained mainly nitrogen which was employed to keep the column operating pressure at a value of 2 bar) and small amounts of light boilers (acetaldehyde (900 vol.-ppm), oxygen (300 vol.-ppm), and propionaldehyde (320 vol.-ppm). This top stream was sent to the flare for disposal.

The sump evaporator was operated by feeding it with a constant amount (5 kg/h) of saturated steam at a pressure of 16 bar. The bottom temperature of the column was 100° C. The bottoms stream, stream S1 of the present invention, mainly consisted of acetonitrile and water, the remainder being high boilers. This stream S1 had an acetonitrile content of about 80 weight-% and a water content of about 20 weight-%.

1.3 Dividing Stream S1 into Streams S2 and S3 (Step (c))

According to present invention, step (c), the stream S1, flow rate 86 kg/h, obtained according to section 1.2 c) above, was divided into two streams, streams S2 (stream (16a according to FIG. 1) and S3 (stream 17 according to FIG. 1). Stream S2 had a flow rate of 84 kg/h and stream S3 had a flow rate of 2 kg/h. Stream S3, 2.3% of stream S1, was subjected to part stream distillation unit G (part stream distillation columns).

1.4 Part-Stream Distillation of Stream S1 (Step (d))

The first fractionation unit, i.e. the first distillation column, G1, had a height of 9.5 m and a diameter of 85 mm and was equipped with 6.5 meters of metal structured Rombopak 9M packing installed in three identical beds. Above the first bed of the structured packing counted from the top, the stream S3 ((stream 17)) was introduced in the first distillation column. The temperature of the stream S3 stream was 60±3° C. The first distillation column was operated at a top pressure of about 1.4 bar and a bottoms temperature of 92±5° C. No reflux was applied. The amount of steam fed to the bottoms evaporator of the first fractionation unit was controlled in such a way that the concentration of acetonitrile in the bottoms was in the range of from 10 to 25 weight-%. The bottoms stream S4b (stream (18b), about 3% of the stream S3) was removed. This stream consisted mainly of water (72-85 weight-%) and acetonitrile (10-24 weight-%). The sum of all the analyzed high-boiling components (27 components) varied in the range of 2-10 weight-%.

The top stream, vapor fraction stream S4a (stream 18a), having a temperature of from 85±3° C., was not condensed and passed to the bottom of the second fractionation unit, i.e. the second distillation column, G2. S4a entered G2 below the last bed of the structured packing counted from the top. G2 had a height of 9.5 m and a diameter of 85 mm and was equipped with 6.5 m of metal structured Rombopak 9M packing installed in 3 identical beds. The second distillation column was operated at a top pressure of about 1.25 bar and a bottoms temperature of 85±5° C. The top stream, vapor fraction stream S4c (stream (18c), at most 1% of the stream S4a), was fully condensed by an external overhead condenser (not shown in FIG. 2) and applied essentially completely to use the condensed, liquid stream as reflux to the second distillation column. The liquid bottoms stream S4 (stream 18), was removed and passed to the next step (recycling of the stream S4). The stream S4 had an acetonitrile content of about 80 weight-% and a water content of about 20 weight-%.

1.5 Recycling of the Stream S4 (Step (4))

a) Preparing a Liquid Stream S5 According to Step (i)

The stream S4, (stream 18 according to FIG. 1 and FIG. 2) was admixed with stream S2 (stream (16a) according to FIG. 1 and FIG. 2). Thus, the stream S4 was pumped back into the bulk process acetonitrile solvent stream. Mixing took place at a point downstream of where stream S3 was diverted from stream S1.

This combined stream having a flow rate of 86 kg/h was mixed with a liquid stream P (referred to as stream (23) in FIG. 1 and FIG. 2) to obtain a stream S5. Stream P was fresh propene stream containing propane (polymer grade, purity>96 weight-%, liquefied under pressure, feed rate: 10 kg/h).

According to this specific embodiment of the present invention, in order to obtain the stream S5, the combined stream of S2 and S4 was further mixed with two other streams: the first one of these streams is stream (19) according to FIG. 1, said stream being obtained from the top of the distillation unit I. The second one of these streams is stream (22) according to FIG. 1, said stream being obtained from the acetonitrile recovery unit J. Both streams (19) and (22) are described in detail hereinunder.

b) Adjusting the Temperature of Stream S5 and Separating Liquid Phases L1 and L2 (Steps (ii) and (iii))

The stream S5 having a flow rate of 150 kg/h±10 kg/h was then fed to a mixer-settler unit operated at 18 bar and a temperature in the range of 15±5° C. The settler tank had a volume of 5.3 liters. Two liquid phases L1 and L2 were obtained, an aqueous phase L2 and an organic phase L1. The upper organic phase L1 was removed from the settler tank as stream (20), the lower aqueous phase L2 was removed from the settler tank as stream (21). The stream (20) had a flow rate in the range of 130 kg/h±13 kg/h.

The stream (20) then was passed to the acetonitrile recycle unit J, the stream (21) was passed to the acetonitrile recovery unit I from which the stream (19) mentioned above was obtained.

The stream (20) thus obtained had an acetonitrile content of about 46 weight-%, a propene content of about 51 weight-% and a water content of about 3 to 4 weight-%.

The stream (21) thus obtained had an acetonitrile content of about 21 weight-%, a water content of about 79 weight-% and a propene content of less than 0.5 weight-%.

c) Acetonitrile Recovery (Acetonitrile Recovery Unit I)

In order to recycle as much solvent as possible, and in order to minimize acetonitrile losses, the stream (21) was introduced into a distillation column from which the stream (19), also referred to as stream TL2, was obtained as top stream which in turn was recycled into the solvent stream as described above.

For this purpose, a distillation column with a height of 9.5 m and a diameter of 100 mm, equipped with 50 bubble trays was used. The column was operated at a top pressure of 1.5 bar with a reflux ratio of 1:4. Stream (21) was fed to the column above bubble tray 26 (counted from the bottom).

The bottoms temperature was about 113° C., and the bottoms product consists mainly of water containing high boiling by-products. A typical composition of the bottoms stream was as follows (weight-% given in parenthesis):water (>99.0), propene glycol (0.5), acetonitrile (at most 0.001), dipropylene glycol (0.06), acetamide (0.01), acetic acid (0.03), TOC (2.4)). After optional metering and analyzing, this stream was discarded.

The overhead product (stream (19)=stream TL2) had the following typical composition ranges (weight-% given in parenthesis):acetonitrile (75-80), water (15-20), low boilers (e.g. propene, 1). As described above stream (19) is recycled to the feed stream which is passed to the mixer-settler unit.

d) Acetonitrile Recycling (Acetonitrile Recycling Unit J), Step (iv)

For acetonitrile recycle, the stream (20) obtained from the mixer-settler unit H was introduced into a distillation column with a height of 10 m and a nominal diameter of 200 mm, equipped with 40 bubble trays. The column was operated at a top pressure of 18 bar with a reflux ratio of 1:4. Stream (20) was fed to the column above bubble tray 26 (counted from the top). The top product (stream (22)), also referred to as stream TL1, containing mainly propene (ca. 97 vol.-%) with small amounts of propane (ca. 1-3 vol.-%) was returned to the feed of the mixer-settler unit H as described above. Thus, excess propene was removed from steam (20) and recycled.

The bottoms stream (stream (2), also referred to as stream BL1), had a temperature in the range of from 106 to 110° C. The precise operation parameters of the column, like energy input in the sump, are adjusted in such a way that the amount of propene returned to the reactor with stream (2) is in a range such that the molar ratio of propene to hydrogen peroxide in stream (1) was about 1:1.3. For the above mentioned feed rate of 15 kg/h of aqueous hydrogen peroxide, this means that the conditions needed to be adjusted such that the flow rate of propene in stream (2) was about 9.7 kg/h.

Prior to feeding stream (2) to the main epoxidation reactor A, acetonitrile (stream (4), chemical grade, from Ineos, purity about 99.9%, containing between 70-180 weight-ppm propionitrile, 5-20 weight-ppm acetamide and <100 weight-ppm water as impurities) was optionally added to compensate for possible solvent losses. The exact amount of additionally added acetonitrile required depended on the losses in exit streams and in by-products but also on the number of samples taken for analytics. A typical amount of additionally added acetonitrile for the above-described process design may be in the range of from 100 to 150 g/h.

Example 2a: Comparative (without Part-Stream Distillation, without Hydrogenation)

The process as described above in Example 1 was first taken into operation using a fresh charge of epoxidation catalyst and fresh acetonitrile (same quality as for make-up stream (4), see section 1.5 d) above) but without using the inventive part-stream distillation. Thus, from stream (16) (stream S1), no stream (17) (stream S3) was separated and subjected to distillation in unit G. Stream 1 was admixed as such with streams (19), (22), and (23).

The starting temperature for the cooling medium loop of the epoxidation main reactor was set at 30° C. At the beginning, the hydrogen peroxide conversion in the epoxidation main reactor A was almost complete. Within 24 hours, the hydrogen peroxide conversion started to decrease, and when it had reached the desired value of approximately 90% (after about 100-200 hours), the temperature of the cooling medium was slowly raised to keep the hydrogen peroxide conversion in the epoxidation main reactor A constant. The rate of the temperature increase of the cooling medium was always less than 1° C./day).

The plant was then operated as described above in Example 1 for 441 h. At the end of this period, the temperature of the cooling medium of the epoxidation main reactor was 35° C. At this point, several components (either by-products of the epoxidation reaction and/or impurities in the feed streams which had not been present at the beginning of the run) had accumulated in the solvent loop. The accumulation increased linearly with no signs of reaching a steady state. The concentration of the components which had accumulated in stream (2), the acetonitrile recycling stream obtained from unit J, after 441 hours on stream is given in Table A. Further, it was found that the stream (2) additionally contained traces of acetaldehyde, propionaldehyde and 2-butanone which also accumulated in the solvent loop, without reaching a steady state.

TABLE A

| Results of Example 2a | |
|---|---|
| Component | Concentration in stream (2) after 440 hours on stream/weight-ppm |
| propionitrile | 44 |
| 4,6-dimethyl-2-heptanol | 390 |
| 2,6-dimethyl-4-heptanol | 815 |
| 2,6-dimethyl-4-heptanone | 14 |
| 4,6-dimethyl-2-heptanone | 8 |
| 1-nitropropane | 29 |
| 2-nitropropane | 45 |

This experiment shows that in the absence of the inventive part-stream distillation, the overall process including solvent recycling suffers from an accumulation of several compounds in the solvent loop. No steady-state was reached relative to the concentration of these compounds.

Example 2b: According to the Invention (with Part-Stream Distillation, without Hydrogenation The run as described in Example 2a was continued, and at t=441 hours on stream, the part-stream distillation (unit G, with the first distillation column G1 and the second distillation column G2) was taken into operation. The run was then continued until a time on stream of 1800 hours was reached. During this period, a stream S3 with a constant flow rate of 2 kg/h (±0.1 kg/h) was diverted from the stream S1 and fed to unit G, corresponding to about 2.3% of the total amount of stream S1. A bottoms stream S4b (stream 18b)) with a constant flow rate of 40 g/h (±10 g/h) was removed at the bottom of the distillation column G1 and discarded. The composition of this bottoms stream after 1800 hours on stream was as follows (weight-% in parenthesis):water (77.5), propene glycol (6.1), acetonitrile (14.1), dipropylene glycol (0.20), tripropylene glycol (0.12), acetamide (0.16), 2,6-dimethyl-4-heptanol (0.16), 4,6-dimethyl-2-heptanol (0.08), 1-nitropropane (0.004), 2-nitropropane (0.004), hydroxyacetone (0.4), acetic acid (0.6), ammonia (0.02), TOC (0.02), acid value=1.4 mg/g (determined according to DIN EN ISO 2114). The concentration of the impurities in the solvent loop (in stream (2) just before starting the part-stream distillation (at 441 hours on stream) and at the end of the run with part-stream distillation (after 1329 hours on stream) is given in Table B.

TABLE B

Results of Example 2b

| Component | Concentration in stream (2)/weight-ppm | | |
|---|---|---|---|
| | Before starting the part-stream distillation (at 440 hours on stream) | At the end of the run (at 1800 hours on stream) | Stationary since/hours on stream |
| propionitrile | 44 | 26 | a) |
| 4,6-dimethyl-2-heptanol | 346 | 48 | 1700 |
| 2,6-dimethyl-4-heptanol | 722 | 20 | a) |
| 2,6-dimethyl-4-heptanone | 13 | 2 | 1700 |
| 4,6-dimethyl-2-heptanone | 7 | 2 | 1700 |
| 1-nitropropane | 26 | 4 | 950 |
| 2-nitropropane | 40 | 8 | 950 | a) Concentration of this component was still falling when the experiment was finished.

At the end of the run, all respective concentrations in stream (2), including the concentrations of acetone, acetaldehyde, propionaldehyde and 2-butanone, not listed in Table B, had reached steady-state, and no accumulation was observed any more. This inventive example clearly shows that making use of the inventive part-stream distillation according to which only a minor fraction of the stream S1 is separated and subjected to distillation, the accumulation of by-products and impurities during solvent recycling can be stopped and a steady-state at very low concentration levels can be reached. Yet further, the example shows that the inventive part-stream distillation method even allows to significantly reduce the concentration of by-products and impurities accumulated in the acetonitrile solvent loop. It also shows that it is sufficient to work-up a small side stream to obtain the desired result, thus offering large savings in energy and investment.

Example 3a: Comparative (without Part-Stream Distillation, with Hydrogenation)

In a new run, the process as described above in Example 1 was first taken into operation using a fresh charge of epoxidation catalyst and fresh acetonitrile (same quality as for make-up stream (4), see section 1.5 d) above) but without using the inventive part-stream distillation. Thus, from stream (16) (stream S1), no stream (17) (stream S3) was diverted and subjected to distillation in unit G. Stream 1 was admixed as such with streams (19), (22), and (23).

In this example, stream (13) (steam S02)) was passed through a hydrogenation reactor (not shown in FIG. 1) located downstream the unit E and upstream the unit F. The hydrogenation reactor was a tubular reactor with a diameter of 53 mm and a height of 3.25 m, filled with a fixed bed catalyst (0.3 weight-% Pd on $Al_2O_3$, strands with 4 mm diameter, HO-13 S4 from BASF SE, operated adiabatically. The reactor was operated as a packed bubble column with gas and liquid flowing in co-current from the bottom to the top of the reactor at a pressure of about 15 bar. Hydrogen was provided was fed at a constant rate of 100 g/h. The temperature of the liquid feed stream (13) to the hydrogenation reactor was adjusted to 70° C. and kept constant throughout the run. At the hydrogenation reactor exit, the pressure was reduced to 1 bar, and the liquid phase and the gas phase leaving the hydrogenation reactor were separated. The gaseous phase was discarded and the liquid phase was fed to unit F as described hereinabove.

The starting temperature for the cooling medium loop of the epoxidation main reactor A was set at 30° C. At the beginning, the hydrogen peroxide conversion in the epoxidation main reactor was almost complete. Within 24 hours, the hydrogen peroxide conversion started to decrease, and when it had reached the desired value of approximately 90% (after about 100-200 hours) the temperature of the cooling medium was slowly raised to keep the hydrogen peroxide conversion in the epoxidation main reactor A constant. The rate of the temperature increase of the cooling medium was always less than 1° C./day).

The plant was then operated as described above in Example 1 for 864 h. At the end of this period, the temperature of the cooling medium of the epoxidation main reactor was 39.2° C. At this point, several components (either by-products of the epoxidation reaction and/or impurities in the feed streams which had not been present at the beginning of the run) had accumulated in the solvent loop. The accumulation increased linearly with no signs of reaching a steady state. The concentration of the components which had accumulated in stream (2), the acetonitrile recycling stream obtained from unit J, after 864 hours on stream is given in Table C. Further, it was found that the stream (2) additionally contained traces of acetone, acetaldehyde, propionaldehyde and 2-butanone which also accumulated in the solvent loop, without reaching a steady state.

TABLE C

Results of Example 3a

| Component | Concentration in stream (2) after 864 hours on stream/weight-ppm |
|---|---|
| propionitrile | 237 |
| 4,6-dimethyl-2-heptanol | 1121 |
| 2,6-dimethyl-4-heptanol | 2168 |
| 2,6-dimethyl-4-heptanone | 23 |
| 4,6-dimethyl-2-heptanone | 20 |
| 1-nitropropane | 204 |
| 2-nitropropane | 229 |

This experiment shows that in the absence of the inventive part-stream distillation, the overall process including solvent recycling suffers from an accumulation of several compounds in the solvent loop. No steady-state was reached relative to the concentration of these compounds.

Example 3b: According to the Invention (with Part-Stream Distillation, with Hydrogenation)

The run as described in Example 3a was continued, and at t=864 hours on stream, the part-stream distillation (unit G) was taken into operation. The run was then continued until a time on stream of 1600 hours was reached.

During this period, a stream S3 with a constant flow rate of 2 kg/h (±0.1 kg/h) was diverted from the stream S1 and fed to the distillation unit G, corresponding to about 2.3% of the total amount of stream S1. A bottoms stream with a constant flow rate of 50 g/h was removed at the bottom of the distillation column G1 and, after being analyzed, was discarded.

The composition of the stream S2 after reaching steady-state was as follows: water (76.1), propene glycol (0.43), propionitrile (0.11), acetonitrile (14.1), dipropylene glycol (0.20), tripropylene glycol (0.13), acetamide (0.17), 2,6-dimethyl-4-heptanol (0.14), 4,6-dimethyl-2-heptanol (0.12), 1-nitropropane (0.10), 2-nitropropane (0.11), hydroxyacetone (0.34), acetic acid (0.46), ammonia (0.03), TOC (0.02), acid value=1.4 mg/g.

The concentration of the impurities in the solvent loop (in stream (2) just before starting the part-stream distillation (at 864 hours on stream) and at the end of the experiment (after 1600 hours on stream) is given in Table D.

TABLE D

Results of Example 3b

| Component | Concentration in stream (2)/weight-ppm | |
|---|---|---|
| | Before starting the part-stream distillation (at 864 hours on stream) | At the end of the run (at 1600 hours on stream) |
| propionitrile | 237 | 139 |
| 4,6-dimethyl-2-heptanol | 1121 | 370 |
| 2,6-dimethyl-4-heptanol | 2168 | 783 |
| 2,6-dimethyl-4-heptanone | 25 | 9 |
| 4,6-dimethyl-2-heptanone | 20 | 5 |
| 1-nitropropane | 204 | 87 |
| 2-nitropropane | 232 | 107 |

Between 1370-1580 hours on stream, all the concentrations in stream (2), including the concentrations of acetone, acetaldehyde, propionaldehyde and 2-butanone, not listed in Table D, had reached steady-state, and no accumulation was observed any more. Until the end of the run no accumulation was observed any more.

This inventive example clearly shows that making use of the inventive part-stream distillation according to which only a minor fraction of the stream S1 is separated and subjected to distillation, the accumulation of by-products and impurities during solvent recycling can be stopped and a steady-state at very low concentration levels can be reached. Yet further, the example shows that the inventive part-stream distillation method even allows to significantly reduce the concentration of by-products and impurities accumulated in the acetonitrile solvent loop. It also shows that it is sufficient to work-up a small side stream to obtain the desired result, thus offering large savings in energy and investment.

Reference Example 1: Preparation of the Epoxidation Catalyst (ZnTiMWW)

1.1 Preparation of Boron-Containing MWW 470.4 kg de-ionized water were provided in a vessel. Under stirring at 70 rpm (rounds per minute), 162.5 kg boric acid were suspended in the water. The suspension was stirred for another 3 h. Subsequently, 272.5 kg piperidine were added, and the mixture was stirred for another hour. To the resulting solution, 392.0 kg Ludox® AS-40 were added, and the resulting mixture was stirred at 70 rpm for another hour. The finally obtained mixture was transferred to a crystallization vessel and heated to 170° C. within 5 h under autogenous pressure and under stirring (50 rpm). The temperature of 170° C. was kept essentially constant for 120 h; during these 120 h, the mixture was stirred at 50 rpm. Subsequently, the mixture was cooled to a temperature of from 50-60° C. within 5 h. The aqueous suspension containing B-MWW had a pH of 11.3 as determined via measurement with a pH electrode. From said suspension, the B-MWW was separated by filtration. The filter cake was then washed with de-ionized water until the washing water had a conductivity of less than 700 microSiemens/cm. The thus obtained filter cake was subjected to spray-drying in a spray-tower with the following spray-drying conditions:

drying gas, nozzle gas: technical nitrogen
temperature drying gas:
temperature spray tower (in): 288-291° C.
temperature spray tower (out): 157-167° C.
temperature filter (in): 150-160° C.
temperature scrubber (in): 40-48° C.
temperature scrubber (out): 34-36° C.
pressure difference filter: 8.3-10.3 mbar
nozzle:
top-component nozzle supplier Gerig; size 0
nozzle gas temperature: room temperature
nozzle gas pressure: 2.5 bar
operation mode: nitrogen straight
apparatus used: spray tower with one nozzle
configuration: spray tower—filter—scrubber
gas flow: 1,900 kg/h
filter material: Nomex® needle-felt 20 m$^2$
dosage via flexible tube pump: SP VF 15 (supplier: Verder)

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening. The spray-dried material was then subjected to calcination at 650° C. for 2 h. The calcined material had a boron (B) content of 1.9 weight-%, a silicon (Si) content of 41 weight-%, and a total organic carbon (TOC) content of 0.18 weight-%.

1.2 Preparation of Deboronated MWW

Based on the spray-dried material obtained according to section 1.1 above, 4 batches of deboronated zeolite MWW were prepared. In each of the first 3 batches, 35 kg of the spray-dried material obtained according to section 1.1 and 525 kg water were employed. In the fourth batch, 32 kg of the spray-dried material obtained according to section 1.1 and 480 kg water were employed. In total, 137 kg of the spray-dried material obtained according to section 1.1 and 2025 kg water were employed. For each batch, the respective amount of water was passed into a vessel equipped with a reflux condenser. Under stirring at 40 r.p.m., the given amount of the spray-dried material was suspended into the water. Subsequently, the vessel was closed and the reflux condenser put into operation. The stirring rate was increased to 70 r.p.m. Under stirring at 70 r.p.m., the content of the vessel was heated to 100° C. within 10 h and kept at this temperature for 10 h. Then, the content of the vessel was cooled to a temperature of less than 50° C. The resulting deboronated zeolitic material of structure type MWW was separated from the suspension by filtration under a nitrogen pressure of 2.5 bar and washed four times with deionized water. After the filtration, the filter cake was dried in a nitrogen stream for 6 h. The deboronated zeolitic material obtained in 4 batches (625.1 kg nitrogen-dried filter cake in total) had a residual moisture content of 79%, as determined using an IR (infrared) scale at 160° C. From the nitrogen-dried filter cake having a residual moisture content of 79% obtained according to section a) above, an aqueous suspension was prepared with deionized water, the suspension having a solid content of 15 weight-%. This suspension was subjected to spray-drying in a spray-tower with the following spray-drying conditions:

drying gas, nozzle gas: technical nitrogen
temperature drying gas:
temperature spray tower (in): 304° C.
temperature spray tower (out): 147-150° C.
temperature filter (in): 133-141° C.
temperature scrubber (in): 106-114° C.
temperature scrubber (out): 13-20° C.
pressure difference filter: 1.3-2.3 mbar
nozzle:
top-component nozzle: supplier Niro, diameter 4 mm
nozzle gas throughput: 23 kg/h
nozzle gas pressure: 2.5 bar
operation mode: nitrogen straight
apparatus used: spray tower with one nozzle
configuration: spray tower—filter—scrubber
gas flow: 550 kg/h
filter material: Nomex® needle-felt 10 m²
dosage via flexible tube pump: VF 10 (supplier: Verder)

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening. The spray-dried MWW material obtained had a B content of 0.08 weight-%, an Si content of 42 weight-%, and a TOC of 0.23 weight-%.

1.3 Preparation of TiMWW

Based on the deboronated MWW material as obtained according to section 1.2 above, a zeolitic material of structure type MWW containing titanium (Ti) was prepared, referred to in the following as TiMWW. The synthesis was performed in two experiments, described in the following as a) and b):

a) First Experiment

| Starting materials: | deionized water: | 244.00 kg |
|---|---|---|
| | piperidine: | 118.00 kg |
| | tetrabutylorthotitanate: | 10.90 kg |
| | deboronated zeolitic material: | 54.16 kg |

54.16 kg of the deboronated zeolitic material of structure type MWW were transferred in to a first vessel A. In a second vessel B, 200.00 kg deionized water were transferred and stirred at 80 r.p.m. 118.00 kg piperidine were added under stirring, and during addition, the temperature of the mixture increased for about 15° C. Subsequently, 10.90 kg tetrabutylorthotitanate and 20.00 kg deionized water were added. Stirring was then continued for 60 min. The mixture of vessel B was then transferred into vessel A, and stirring in vessel A was started (70 r.p.m.). 24.00 kg deionized water were filled into vessel A and transferred to vessel B. The mixture in vessel B was then stirred for 60 min. at 70 r.p.m. At the beginning of the stirring, the pH of the mixture in vessel B was 12.6, as determined with a pH electrode. After said stirring at 70 r.p.m., the frequency was decreased to 50 r.p.m., and the mixture in vessel B was heated to a temperature of 170° C. within 5 h. At a constant stirring rate of 50 r.p.m., the temperature of the mixture in vessel B was kept at an essentially constant temperature of 170° C. for 120 h under autogenous pressure. During this crystallization of TiMWW, a pressure increase of up to 10.6 bar was observed. Subsequently, the obtained suspension containing TiMWW having a pH of 12.6 was cooled within 5 h. The cooled suspension was subjected to filtration, and the separated mother liquor was transferred to waste water discharge. The filter cake was washed four times with deionized water under a nitrogen pressure of 2.5 bar. After the last washing step, the filter cake was dried in a nitrogen stream for 6 h. From 246 kg of said filter cake, an aqueous suspension was prepared with deionized water, the suspension having a solid content of 15 weight-%. This suspension was subjected to spray-drying in a spray-tower with the following spray-drying conditions:

drying gas, nozzle gas: technical nitrogen
temperature drying gas:
temperature spray tower (in): 304° C.
temperature spray tower (out): 147-152° C.
temperature filter (in): 133-144° C.
temperature scrubber (in): 111-123° C.
temperature scrubber (out): 12-18° C.
pressure difference filter: 1.8-2.8 mbar
nozzle:
top-component nozzle: supplier Niro, diameter 4 mm
nozzle gas throughput: 23 kg/h
nozzle gas pressure: 2.5 bar
operation mode: nitrogen straight
apparatus used: spray tower with one nozzle
configuration: spray tower—filter—scrubber
gas flow: 550 kg/h
filter material: Nomex® needle-felt 10 m²
dosage via flexible tube pump: VF 10 (supplier: Verder)

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening. The spray-dried TiMWW material obtained from the first experiment had a Si content of 37 weight-%, a Ti content of 2.4 weight-%, and a TOC of 7.5 weight-%.

b) Second Experiment

The second experiment was carried out in the same way as the first experiment described in section a) above. The spray-dried TiMWW material obtained from the second experiment had a Si content of 36 weight-%, a Ti content of 2.4 weight-%, a TOC of 8.0 weight-%

1.4 Acid Treatment of TiMWW

Each of the two spray-dried TiMWW materials as obtained in the first and the second experiment described in sections 1.3 a) and 1.3 b) above was subjected to acid treatment as described in the following in sections a) and b). In section c) hereinunder, it is described how a mixture of the materials obtained from a) and b) are spray-dried. In section d) hereinunder, it is described how the spray-dried material is calcined.

a) Acid Treatment of the Spray-Dried Material Obtained According to Section 1.3.a)

| Starting materials: | deionized water: | 690.0 kg |
|---|---|---|
| | nitric acid: (53%): | 900.0 kg |
| | spray-dried Ti-MWW 1.3. a): | 53.0 kg |

670.0 kg deionized water were filled in a vessel. 900 kg nitric acid were added, and 53.0 kg of the spray-dried TiMWW were added under stirring at 50 r.p.m. The resulting mixture was stirred for another 15 min. Subsequently, the stirring rate was increased to 70 r.p.m. Within 1 h, the mixture in the vessel was heated to 100° C. and kept at this temperature and under autogenous pressure for 20 h under stirring. The thus obtained mixture was then cooled within 2 h to a temperature of less than 50° C. The cooled mixture was subjected to filtration, and the filter cake was washed six times with deionized water under a nitrogen pressure of 2.5 bar. After the last washing step, the filter cake was dried in a nitrogen stream for 10 h. The washing water after the sixth washing step had a pH of about 2.7. 225.8 kg dried filter cake were obtained.

b) Acid Treatment of the Spray-Dried Material Obtained According to Section 1.3.b)

| Starting materials: | deionized water: | 690.0 kg |
|---|---|---|
| | nitric acid: (53%): | 900.0 kg |
| | spray-dried Ti-MWW 1.3. b): | 55.0 kg |

The acid treatment of the spray-dried material obtained according to section 1.3.b) was carried in the same way as the acid treatment of the spray-dried material obtained according to section 1.3.a) as described in section 1.4 a). The washing water after the sixth washing step had a pH of about 2.7. 206.3 kg dried filter cake were obtained.

c) Spray-Drying of the Mixture of the Materials Obtained from 1.4.a) and 1.4 b)

From 462.1 kg of the mixture of the filter cakes obtained from 1.4.a) and 1.4 b), an aqueous suspension was prepared with deionized water, the suspension having a solid content of 15 weight-%. This suspension was subjected to spray-drying in a spray-tower with the following spray-drying conditions:

drying gas, nozzle gas: technical nitrogen
temperature drying gas:
temperature spray tower (in): 304-305° C.
temperature spray tower (out): 151° C.
temperature filter (in): 141-143° C.
temperature scrubber (in): 109-118° C.
temperature scrubber (out): 14-15° C.
pressure difference filter: 1.7-3.8 mbar
nozzle:
top-component nozzle: supplier Niro, diameter 4 mm
nozzle gas throughput: 23 kg/h
nozzle gas pressure: 2.5 bar
operation mode: nitrogen straight
apparatus used: spray tower with one nozzle
configuration: spray tower—filter—scrubber
gas flow: 550 kg/h
filter material: Nomex® needle-felt 10 m$^2$
dosage via flexible tube pump: VF 10 (supplier: Verder)

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening. The spray-dried acid-treated TiMWW material had a Si content of 42 weight-%, a Ti content of 1.6 weight-%, and a TOC content of 1.7 weight-%.

d) Calcination of the Spray-Dried Material Obtained According to 1.4.c)

The spray-dried material was then subjected to calcination at 650° C. in a rotary furnace for 2 h. The calcined material had a Si content of 42.5 weight-%, a Ti content of 1.6 weight-% and a TOC content of 0.15 weight-%.

1.5 Impregnation of TiMWW with Zn

The acid-treated, spray-dried and calcined material as obtained according to 1.4 d) was then subjected to an impregnation stage.

| Starting materials: | deionized water: | 2610.0 kg |
|---|---|---|
| | zinc acetate dihydrate: | 15.93 kg |
| | calcined Ti-MWW 1.4.d): | 87.0 kg |

Impregnation was carried out in 3 batches a) to c) as follows:

a) In a vessel equipped with a reflux condenser, a solution of 840 kg deionized water and 5.13 kg zinc acetate dihydrate was prepared within 30 min. Under stirring (40 r.p.m.), 28 kg of the calcined Ti-MWW material obtained according to 1.4.d) were suspended. Subsequently, the vessel was closed and the reflux condenser put into operation. The stirring rate was increased to 70 r.p.m.

b) In a vessel equipped with a reflux condenser, a solution of 840 kg deionized water and 5.13 kg zinc acetate dihydrate was prepared within 30 min. Under stirring (40 r.p.m.), 28 kg of the calcined Ti-MWW material obtained according to 1.4.d) were suspended. Subsequently, the vessel was closed and the reflux condenser put into operation. The stirring rate was increased to 70 r.p.m.

c) In a vessel equipped with a reflux condenser, a solution of 930 kg deionized water and 5.67 kg zinc acetate dihydrate was prepared within 30 min. Under stirring (40 r.p.m.), 31 kg of the calcined Ti-MWW material obtained according to 1.4.d) were suspended. Subsequently, the vessel was closed and the reflux condenser put into operation. The stirring rate was increased to 70 r.p.m.

In all batches a) to c), the mixture in the vessel was heated to 100° C. within 1 h and kept under reflux for 4 h a t a stirring rate of 70 r.p.m. Then, the mixture was cooled within 2 h to a temperature of less than 50° C. For each batch a) to c), the cooled suspension was subjected to filtration, and the mother liquor was transferred to waste water discharge. The filter cake was washed five times with deionized water under a nitrogen pressure of 2.5 bar. After the last washing step, the filter cake was dried in a nitrogen stream for 10 h. For batch a), 106.5 kg nitrogen-dried filter cake were finally obtained. For batch b), 107.0 kg nitrogen-dried filter cake were finally obtained. For batch c), 133.6 kg nitrogen-dried filter cake were finally obtained. The thus dried Zn-impregnated TiMWW material (ZnTiMWW), for each batch, had a Si content of 42 weight-%, a Ti content of 1.6 weight-%, a Zn content of 1.4 weight-% and a TOC of 1.4 weight-%.

1.6 Preparation of a Micropowder

From 347.1 kg of the mixture of the filter cakes obtained according to 1.5 above, an aqueous suspension was prepared with deionized water, the suspension having a solid content of 15 weight-%. This suspension was subjected to spray-drying in a spray-tower with the following spray-drying conditions:

apparatus used: spray tower with one nozzle
operation mode: nitrogen straight
configuration: dehumidifier—filter—scrubber
dosage: flexible-tube pump VF 10 (supplier: Verder)
 nozzle with a diameter of 4 mm (supplier: Niro)
filter material: Nomex® needle-felt 10 m$^2$

|  |  | Runtime/h | | | | |
|---|---|---|---|---|---|---|
|  |  | 0.5 | 1.5 | 2.5 | 3.5 | 4.5 |
| Flow rate gas/(kg/h) | | 550 | 550 | 550 | 550 | 550 |
| Temperature drying gas/° C. | spray tower (in) | 305 | 305 | 305 | 305 | 305 |
| | spray tower (out) | 151 | 151 | 151 | 151 | 151 |
| | Filter (in) | 140 | 137 | 130 | 127 | 126 |
| | Scrubber (in) | 110 | 110 | 110 | 108 | 105 |
| | Scrubber (out) | 14 | 14 | 15 | 15 | 15 |
| Differential pressure/mbar | spray tower | 3.1 | 3 | 3 | 2.8 | 2.9 |
| | Filter | 1.7 | 1.7 | 1.8 | 1.8 | 2.1 |
| | Scrubber | 3.8 | 4.1 | 4.2 | 4.2 | 4.2 |
| Pressure/mbar | spray tower | −103 | −1.2 | −0.9 | −0.9 | −1.1 |
| Nozzle gas | Flow rate kg/h | 23 | 23 | 23 | 23 | 23 |
| | Temperature/° C. | r.t.*) | r.t.*) | r.t.*) | r.t.*) | r.t.*) |
| | Pressure/bar | 2.5 | 2.5 | 2.5 | 2.5 | 2.5 |
| Spray-dried product | Temperature/° C. | r.t.*) | r.t.*) | r.t.*) | r.t.*) | r.t.*) |

*)room temperature

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening. The spray-dried material thus obtained had a Zn content of 1.4 weight-%, a Ti content of 1.7 weight-%, a Si content of 40 weight-%, and a TOC content of 0.27 weight-%. The spray-dried product was then subjected to calcination for 2 h at 650° C. under air in a rotary furnace, yielding 76.3 kg of calcined spray-dried ZnTiMWW. The calcined spray-dried material thus obtained had a Zn content of 1.4 weight-%, a Ti content of 1.7 weight-%, a Si content of 42 weight-%, and a C content of 0.14 weight-%. The bulk density of the calcined spray-dried ZnTiMWW was 90 g/l (gram/liter).

1.7 Preparation of a Molding

Starting from the calcined spray-dried ZnTiMWW material obtained according to section 1.6 above, a molding was prepared, dried, and calcined. Therefor, 22 batches were prepared, each starting from 3.4 kg of the calcined spray-dried ZnTiMWW material obtained in Example 1, 0.220 kg Walocel™ (Walocel MW 15000 GB, Wolff Cellulosics GmbH & Co. KG, Germany), 2.125 kg Ludox® AS-40 and 6.6 l deionized water, as follows: 3.4 kg ZnTiMWW and 0.220 kg Walocel were subjected to kneading in an edge mill for 5 min. Then, during further kneading, 2.125 kg Ludox were added continuously. After another 10 min, addition of 6 l of deionized water was started. After another 30 min, further 0.6 l of deionized water were added. After a total time of 50 min, the kneaded mass had become extrudable. Thereafter, the kneaded mass was subjected to extrusion under 65-80 bar wherein the extruder was cooled with water during the extrusion process. Per batch, the extrusion time was in the range of from 15 to 20 min. The power consumption per batch during extrusion was 2.4 A. A die head was employed allowing for producing cylindrical strands having a diameter of 1.7 mm. At the die head out outlet, the strands were not subjected to a cutting to length. The strands thus obtained were dried for 16 h at 120° C. in a drying chamber under air. In total (sum of the 22 batches), 97.1 kg white strands with a diameter of 1.7 mm were obtained. 65.5 kg of the dried strands were subjected to calcination in a rotary furnace at 550° C. for 1 h under air, yielding 62.2 kg calcined strands. Thereafter, the strands were sieved (mesh size 1.5 mm), and the yield, after sieving, was 57.7 kg. The thus obtained moldings exhibited a bulk density of 322 g/l (gram per liter) and had a Zn content of 1.2 weight-%, a Ti content of 1.4 weight-%, a Si content of 43 weight-%, and a C content of 0.13 weight-%. The sodium (Na) content was 0.07 weight-%.

1.8 Post-Treatment of the Molding

Starting from the calcined strands obtained according to 1.7 above, a post-treatment stage was performed as follows: 590 kg deioinized water were filled in a vessel. Then, 29.5 kg of the calcined moldings obtained according to section 1.7 above were added. The vessel was closed (pressure-tight), and the obtained mixture was heated to a temperature of 145° C. within 1.5 h and kept at this temperature under autogenous pressure (about 3 bar) for 8 h. Then, the mixture was cooled for 2 h. The water-treated strands were subjected to filtration and washed with deionized water. The obtained strands were heated in a drying chamber under air within 1 h to a temperature of 120° C. and kept at this temperature for 16 h. Subsequently, the dried material was heated under air to a temperature of 450° C. within 5.5 h and kept at this temperature for 2 h. Thereafter, the strands were sieved (mesh size 1.5 mm), and the yield, after sieving, was 27.5 kg. The thus obtained water-treated moldings exhibited a bulk density of 340 g/l (gram per liter) and had a Zn content of 1.3 weight-%, a Ti content of 1.4 weight-%, a Si content of 43 weight-%, and a C content of 0.10 weight-%.

Reference Example 2: Determination of Dv10, Dv50, and Dv90 Values

1. Sample Preparation: 1.0 g of the micropowder is suspended in 100 g deionized water and stirred for 1 min.
2. Apparatus and respective parameters used:
   Mastersizer S long bed version 2.15, ser. No. 33544-325; supplier: Malvern Instruments GmbH, Herrenberg, Germany
   focal width: 300RF mm
   beam length: 10.00 mm
   module: MS17
   shadowing: 16.9%
   dispersion model: 3$$D
   analysis model: polydisperse
   correction: none

Reference Example 3: Determination of the Silanol Concentration

For the determination of the silanol concentration, the $^{29}Si$ MAS NMR experiments were carried out at room temperature on a VARIAN Infinityplus-400 spectrometer using 5.0 mm $ZrO_2$ rotors. The $^{29}Si$ MAS NMR spectra were collected at 79.5 MHz using a 1.9 microseconds pi/4 pulse with 10 s recycle delay and 4000 scans. All $^{29}Si$ spectra were recorded on samples spun at 6 kHz, and chemical shifts were referenced to 4,4-dimethyl-4-silapentane sulfonate sodium (DSS). For the determination of the silanol group concentration, a given $^{29}Si$ MAS NMR spectrum is deconvolved by the proper Gaussian-Lorentzian line shapes. The concentration of the silanol groups with respect to the total number of Si atoms is obtained by integrating the deconvolved $^{29}Si$ MAS NMR spectra.

Reference Example 4: Determination of the Crush Strength of the Moldings

The crush strength as referred to in the context of the present invention is to be understood as determined via a crush strength test machine Z2.5/TS1S, supplier Zwick GmbH & Co., D-89079 Ulm, Germany. As to fundamentals of this machine and its operation, reference is made to the respective instructions handbook "Register 1: Betriebsanleitung/Sicherheitshandbuch für die Material-Prüfmaschine Z2.5/TS1S", version 1.5, December 2001 by Zwick GmbH & Co. Technische Dokumentation, August-Nagel-Strasse 11, D-89079 Ulm, Germany. With said machine, a given strand as described in Reference Example 1 is subjected to an increasing force via a plunger having a diameter of 3 mm until the strand is crushed. The force at which the strand crushes is referred to as the crushing strength of the strand. The machine is equipped with a fixed horizontal table on which the strand is positioned. A plunger which is freely movable in vertical direction actuates the strand against the fixed table. The apparatus was operated with a preliminary force of 0.5 N, a shear rate under preliminary force of 10 mm/min and a subsequent testing rate of 1.6 mm/min. The vertically movable plunger was connected to a load cell for force pick-up and, during the measurement, moved toward the fixed turntable on which the molding (strand) to be investigated is positioned, thus actuating the strand against the table. The plunger was applied to the stands perpendicularly to their longitudinal axis. Controlling the experiment was carried out by means of a computer which registered and evaluated the results of the measurements. The values obtained are the mean value of the measurements for 10 strands in each case.

Reference Example 5: $^{29}Si$ Solid-State NMR Spectra Regarding $Q^3$ and $Q^4$ Structures All $^{29}Si$ solid-state NMR experiments were performed using a Bruker Avance spectrometer with 300 MHz $^1H$ Larmor frequency (Bruker Biospin, Germany). Samples were packed in 7 mm $ZrO_2$ rotors, and measured under 5 kHz Magic Angle Spinning at room temperature. $^{29}Si$ direct polarization spectra were obtained using (pi/2)-pulse excitation with 5 microsecond pulse width, a $^{29}Si$ carrier frequency corresponding to −65 ppm in the spectrum, and a scan recycle delay of 120 s. Signal was acquired for 25 ms under 45 kHz high-power proton decoupling, and accumulated over 10 to 17 hours. Spectra were processed using Bruker Topspin with 30 Hz exponential line broadening, manual phasing, and manual baseline correction over the full spectrum width. Spectra were referenced with the polymer Q8M8 as an external secondary standard, setting the resonance of the trimethylsilyl M group to 12.5 ppm. The spectra were then fitted with a set of Gaussian line shapes, according to the number of discernable resonances. Relating to the presently assessed spectra, 6 lines in total were used, accounting for the five distinct peak maxima (at approximately −118, −115, −113, −110 and −104 ppm) plus a clearly visible shoulder at −98 ppm. Fitting was performed using DMFit (Massiot et al., Magnetic Resonance in Chemistry, 40 (2002) pp 70-76). Peaks were manually set at the visible peak maxima or shoulder. Both peak position and line width were then left unrestrained, i.e., fit peaks were not fixed at a certain position. The fitting outcome was numerically stable, i.e., distortions in the initial fit setup as described above did lead to similar results. The fitted peak areas were further used normalized as done by DMFit. For the quantification of spectrum changes, a ratio was calculated that reflects changes in the peak areas "left hand" and "right hand", as follows. The six peaks as described were labeled with 1, 2, 3, 4, 5, and 6, and the ratio Q was calculated with the formula $100*\{[a_1-a_2]/[a_4-a_5-a_6]\}/a_3$. In this formula, $a_{i,\ i=1,6}$ represents the area of the fitted peak to which this number was attributed.

Reference Example 6: Water Adsorption/Desorption

The water adsorption/desorption isotherms measurements were performed on a VTI SA instrument from TA Instruments following a step-isotherm program. The experiment consisted of a run or a series of runs performed on a sample material that has been placed on the microbalance pan inside of the instrument. Before the measurement were started, the residual moisture of the sample was removed by heating the sample to 100° C. (heating ramp of 5° C./min) and holding it for 6 h under a $N_2$ flow. After the drying program, the temperature in the cell was decreased to 25° C. and kept isothermal during the measurements. The microbalance was calibrated, and the weight of the dried sample was balanced (maximum mass deviation 0.01 wt. %). Water uptake by the sample was measured as the increase in weight over that of the dry sample. First, an adsorption curve was measured by increasing the relative humidity (RH) (expressed as weight-% water in the atmosphere inside of the cell) to which the samples was exposed and measuring the water uptake by the sample at equilibrium. The RH was increased with a step of 10 wt. % from 5 to 85% and at each step the system controlled the RH and monitored the sample weight until reaching the equilibrium conditions and recording the weight uptake. The total adsorbed water amount by the sample was taken after the sample was exposed to the 85 weight-% RH. During the desorption measurement the RH was decreased from 85 wt. % to 5 wt. % with a step of 10% and the change in the weight of the sample (water uptake) was monitored and recorded.

Reference Example 7: FT-IR Measurements

The FT-IR (Fourier-Transformed-Infrared) measurements were performed on a Nicolet 6700 spectrometer. The molding was powdered and then pressed into a self-supporting pellet without the use of any additives. The pellet was introduced into a high vacuum (HV) cell placed into the FT-IR instrument. Prior to the measurement the sample was pretreated in high vacuum ($10^{-5}$ mbar) for 3 h at 300° C. The spectra were collected after cooling the cell to 50° C. The spectra were recorded in the range of 4000 to 800 $cm^{-1}$ at a resolution of 2 $cm^{-1}$. The obtained spectra are represented in a plot having on the x axis the wavenumber ($cm^{-1}$) and on the y axis the absorbance (arbitrary units, a.u.). For the quantitative determination of the peak heights and the ratio between these peaks a baseline correction was carried out. Changes in the 3000 to 3900 $cm^{-1}$ region were analyzed and for comparing multiple samples, a reference band at 1880±5 $cm^{-1}$ was taken.

Reference Example 8: Definition and Determination of the Octanol-Water Partition Coefficient $K_{OW}$ The octanol-water partition coefficient $K_{OW}$ of a given compound is defined as the ratio of said compound's chemical concentration in the octanol phase relative to said compound's chemical concentration in the aqueous phase in a two-phase system of 1-octanol and water at a temperature of 25° C.

The octanol-water partition coefficient $K_{OW}$ of a given compound is determined using the shake-flask method which consists of dissolving the compound in a volume of high-purity 1-octanol and deionized water (pre-mixed and calibrated for at least 24 h) and measuring the concentration of the compound in each the 1-octanol phase and the water phase by a sufficiently exact method, preferably via UV/VIS spectroscopy. This method is described in the OECD Guideline for the testing of chemicals, number 107, adopted on Jul. 27, 1995.

DESCRIPTION OF THE FIGURES

In FIG. 1, the letters and numbers have the following meanings:
  A epoxidation unit
  B distillation unit
  C epoxidation unit
  D distillation unit
  E distillation unit
  F distillation unit
  G part stream distillation unit
  H mixer-settler unit
  I acetonitrile recovery unit
  J acetonitrile recycle unit
  (1)-(23) streams according to a specifically preferred process as described in the examples
  S0, S01, S02, S1, S2, S3, S4, S4b, S5, L1, L2, TL1, TL2, TL2, BL2 streams according to a preferred process as described in the general description and the examples
In FIG. 1, the letters and numbers have the following meanings:
  G1 first fractionation unit of the part stream distillation unit G
  G2 second fractionation unit of the part stream distillation unit G
  (16), (16a), (17), (18), (18a), (18b), (18c), (19), (22), (23) streams according to a specifically preferred process as described in the examples
  S1, S2, S3, S4, S4a, S4b, S4c, S5, TL2
    streams according to a preferred process as described in the general description and the examples

CITED PRIOR ART

Figure 1:
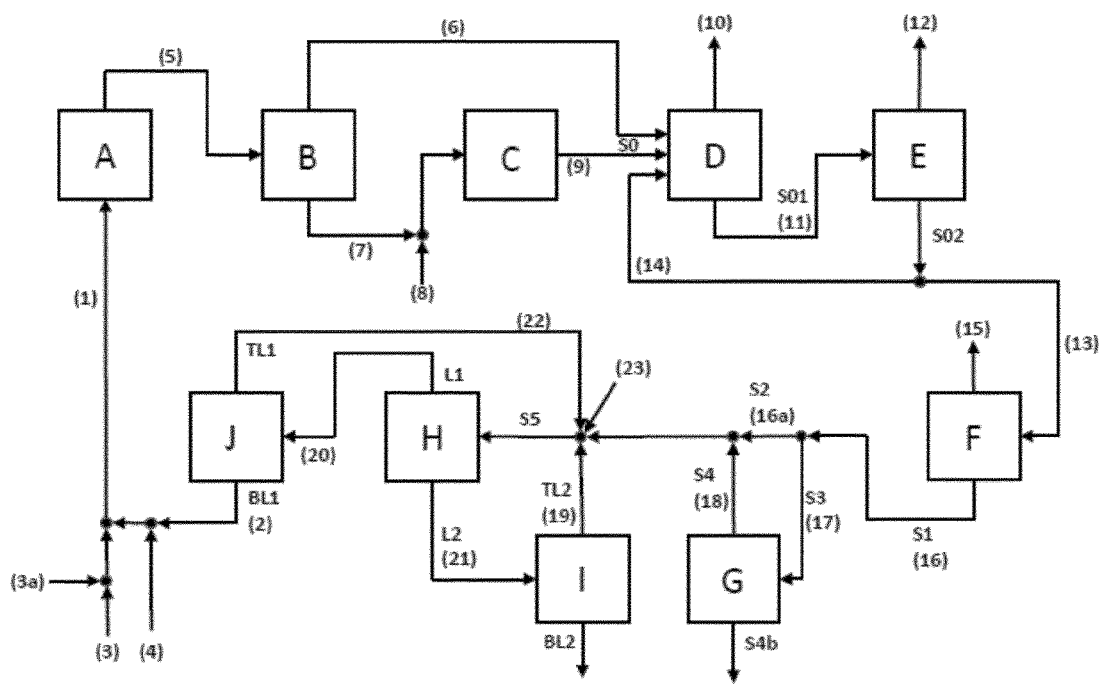
FIG. 1 shows a block diagram of a preferred process of the present invention.
Figure 2:
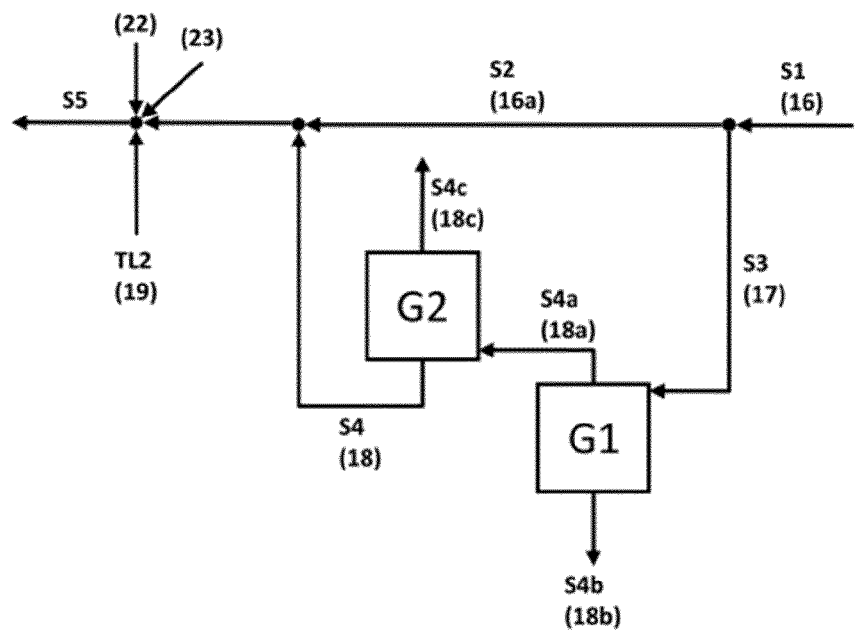
FIG. 2 shows a block diagram the part stream distillation G of FIG. 1 unit in detail.

WO 2011/006990 A1
US 2007043226 A1
WO 2007/000396 A1
EP 0 427 062 A2
U.S. Pat. No. 5,194,675
US 2004068128 A1
K. J. Lissant, Making and Breaking Emulsions, Res. Lab., Petrolite Corp., St. Louis, Mo., USA, in: K. J. Lissant (ed.), Emulsion Technology (1974), chapter 2, pp 111-124, Dekker, N.Y.
S. E. Taylor, Chem. Ind. (1992), pp 770-773

The invention claimed is:

1. A continuous process for the preparation of propylene oxide, comprising
  (a) reacting propene, optionally admixed with propane, with hydrogen peroxide in a reaction apparatus in the presence of acetonitrile as solvent, obtaining a stream S0 leaving the reaction apparatus, S0 containing propylene oxide, acetonitrile, water, at least one further component B, optionally propene and optionally propane, wherein the normal boiling point of the at least one component B is higher than the normal boiling point of acetonitrile and wherein the decadic logarithm of the octanol-water partition coefficient (log $K_{OW}$) of the at least one component B is greater than zero;
  (b) separating propylene oxide from S0, optionally after having separated propene and optionally propane, obtaining a stream S1 containing acetonitrile, water and the at least one further component B;
  (c) dividing S1 into two streams S2 and S3, wherein the total weight of S3 relative to the total weight of S1 is in the range of from 0.01 to 25%;
  (d) subjecting S3 to a vapor-liquid fractionation in a first fractionation unit, obtaining a vapor fraction stream S4a being depleted, relative to S3, of at least one of the at least one component B and obtaining a liquid bottoms stream S4b, and subjecting at least part of the vapor fraction stream S4a to a vapor-liquid fractionation in a second fractionation unit, obtaining a vapor fraction stream S4c and a liquid bottoms stream S4 being depleted, relative to S4a, of at least one of the at least one component B;
  (e) recycling at least a portion of S4, optionally after work-up, to (a), and recycling at least a portion of S2, optionally after work-up, to (a).

2. The process of claim 1, wherein in (c), the total weight of S3 relative to the total weight of S1 is in the range of from 0.05 to 20%.

3. The process of claim 1, wherein from 90 to 99.9 weight-% of S1 consist of acetonitrile and water and wherein from 0.01 to 5 weight-% of S1 consist of the at least one component B.

4. The process of claim 1, wherein S3 is fed to the top of the first fractionation unit and the at least part of the vapor fraction stream S4a is fed to the bottom of the second fractionation unit, wherein in (d), the first fractionation unit is operated at an absolute pressure at the top of the first fractionation unit in the range of from 0.5 to 5 bar and wherein the second fractionation unit is operated at an absolute pressure in the bottom of the second fractionation unit in the range of from 65 to 95% of the pressure at the top of the first fractionation unit.

5. The process of claim 1, wherein in (d), the number of theoretical trays of the first fractionation unit is in the range of from 1 to 100 and the number of theoretical trays of the second fractionation unit is in the range of from 1 to 100.

6. The process of claim 1, wherein in (d), the first fractionation unit is operated without reflux, the at least part of the vapor fraction stream S4a subjected to the vapor-liquid fractionation in the second fractionation unit not being condensed prior to subjecting to the vapor-liquid fractionation in the second fractionation unit, and the second fractionation unit is operated with reflux, wherein a fraction of the vapor fraction stream S4c is used, after condensation, as reflux and wherein the reflux ratio is in the range of from 0.5:1 to 1:1.

7. The process of claim 1, wherein from 10 to 30 weight-% of the liquid bottoms stream S4b consist of acetonitrile and from 0.1 to 10 weight-% of the liquid bottoms stream S4b consist of the at least one further component B.

8. The process of claim 1, wherein from 90 to 99.99 weight-% of S4 consist of acetonitrile and water, and wherein from 0.0001 to 0.2 weight-% of S4 consist of the at least one component B.

9. The process of claim 1, wherein (e) comprises working-up S4, said working-up comprising combining at least a portion of S4 with S2 obtaining a liquid stream.

10. The process of claim 9, wherein (e) comprises subjecting the liquid stream to acetonitrile-water separation obtaining a stream enriched in acetonitrile, and recycling said stream enriched in acetonitrile, optionally after further work-up, to (a).

11. The process of claim 10, wherein (e) comprises
(i) preparing a liquid stream S5 by adding a liquid stream P to S2, or to at least the portion of S4, or to the liquid stream obtained from combining S2 and at least the portion of S4,
wherein P comprises at least 95 weight-% of C3, based on the total weight of P,
wherein C3 is propene optionally admixed with propane with a minimum weight ratio of propene relative to propane of 7:3, and
wherein P is added in an amount so that in S5, the weight ratio of C3 relative to acetonitrile is in the range of from 0.2:1 to 5:1;
(ii) subjecting S5 to a temperature of 92° C. at most and a pressure of at least 10 bar, obtaining a first liquid phase L1 and a second liquid phase L2,
wherein at least 95 weight-% of L1 consist of C3, acetonitrile, water and the at least one component B, the water content of L1 being less than 10 weight % based on the total weight of L1, and
wherein at least 95 weight-% of L2 consist of C3, acetonitrile, water and the at least one component B, the C3 content of L2 being 5 weight-% at most, based on the total weight of L2, and the acetonitrile content of L2 being less than 45 weight-% based on the total weight of L2;
(iii) separating L1 from L2;
(iv) recycling L1 as the stream enriched in acetonitrile, optionally after further work-up, to (a).

12. The process of claim 11, further comprising working up L1, said working-up comprising subjecting L1 to a distillation stage wherefrom a bottoms stream BL1 is obtained, wherein at least 95 weight-% of BL1 consist of C3, acetonitrile, water and the at least one component B, wherein the C3 content of BL1 is in the range of from 7 to 18 weight-%, and recycling BL1 as the stream enriched in acetonitrile, optionally without any further work-up, to (a).

13. The process of claim 12, wherein from 0.01 to 5 weight-%, of BL1 consist of the at least one component B.

14. The process of claim 1, wherein (b) comprises
(I) separating propene, optionally together with propane, and oxygen which is optionally additionally contained in S0, from S0, obtaining a stream S01 enriched in propylene oxide, acetonitrile, water, and the at least one component B, wherein at least 99 weight-% of S01 consist of acetonitrile, water, the at least one component B and propylene oxide; wherein for separation, a fractionation unit is used, wherein at the top of the fractionation unit, liquid acetonitrile, optionally admixed with liquid water, is added as entraining agent;
(II) separating propylene oxide from S01, obtaining a stream S02 enriched in acetonitrile, water and the at least one component B, wherein at least 95 weight-% of S02 consist of acetonitrile, water and the at least one component B, and wherein the weight ratio of acetonitrile relative to water is greater than 1:1, wherein S02 is subjected to (c) as S1.

15. The process of claim 14, wherein (b) further comprises
(IIIa) subjecting S02 obtained from (II) to hydrogenation; and/or
(IIIb) subjecting the stream obtained from (II) or (IIIa) to distillation to obtain a bottoms stream,
wherein the hydrogenated stream obtained from (IIIa) or the bottoms stream obtained from (IIIb) is subjected to (c) as S1.

16. The process of claim 1, wherein in (a), propene is reacted with hydrogen peroxide in the presence of a heterogeneous catalyst, said heterogeneous catalyst comprising a zeolite.

17. The process of claim 1, wherein from 90 to 97 weight-% of S0 consist of acetonitrile, water, and propylene oxide, and wherein from 0.01 to 3 weight-% of S0 consist of the at least one component B.

18. The process of claim 1, wherein the at least one component B is propionitrile, 1-nitropropane, 2-nitropropane, 3-methylbutanenitrile, n-pentanenitrile, 1-pentanol, 2-pentanol, 2-butanone, 2-pentanone, 2-hexanone, 4-methyl-2-heptanone, 2,6-dimethyl-4-heptanol, 4,6-dimethyl-2-heptanol, 2,6-dimethyl-4-heptanone, 4,6-dimethyl-2-heptanone, 2,6-dimethyl-4,6-heptandiol, 2,4-dimethyloxazoline, 2,5-dimethyloxazoline, cis-2,4-dimethyl-1,3-dioxolane, trans-2,4-dimethyl-1,3-dioxolane, acetaldehyde, propionaldehyde, at least one impurity contained in the hydrogen peroxide employed in (a), or a combination of two or more of these compounds.

19. The process of claim 18, wherein the at least one component B comprises a combination of propionitrile, 1-nitropropane, 2-nitropropane, 2,6-dimethyl-4-heptanol, 4,6-dimethyl-2-heptanol, 2,6-dimethyl-4-heptanone, acetaldehyde, and propionaldehyde.

20. The process of claim 18, wherein in (d), the stream S3 is subjected to a vapor-liquid fractionation in a first fractionation unit, obtaining a vapor fraction stream S4a being depleted, relative to S3, of at least one of the at least one component B, the at least one of the at least one component B comprising propionitrile, or 1-nitropropane, or 2-nitropropane, or 2,6-dimethyl-4-heptanol, or 4,6-dimethyl-2-heptanol, or 2,6-dimethyl-4-hepta-none, or a combination of two or more thereof, and obtaining a liquid bottoms stream S4b, wherein at least part of the vapor fraction stream S4a is subjected to a vapor-liquid fractionation in a second fractionation unit, obtaining a vapor fraction stream S4c and a liquid bottoms stream S4 being depleted, relative to S4a, of at least one of the at least one component B, the at least one of the at least one component B comprising acetaldehyde, or propionaldehyde, or 2-butanone, or a combination of two or more thereof.

21. The process of claim 18, wherein the at least one impurity contained in the hydrogen peroxide employed in (a) is selected from the group of compounds consisting of an alkyl phosphate, a nonyl alcohol, an alkylcyclohexanol ester, an N,N-dialkyl carbonamide, an N-alkyl-N-aryl carbonamide, an N,N-dialkyl carbamate, a tetraalkyl urea, a cycloalkyl urea, a phenylalkyl urea, an N-alkyl-2-pyrrolidone, an N-alkyl caprolactam, and a combination of two or more of these compounds.

22. The process of claim 1, wherein in (d), 90 to 100 weight-% of the vapor fraction stream S4a are subjected to the vapor-liquid fractionation in the second fractionation unit.

* * * * *

UNITED STATES PATENT AND TRADEMARK OFFICE
CERTIFICATE OF CORRECTION

PATENT NO.        : 10,316,007 B2
APPLICATION NO.   : 15/521924
DATED             : June 11, 2019
INVENTOR(S)       : Joaquim Henrique Teles et al.

Page 1 of 1

It is certified that error appears in the above-identified patent and that said Letters Patent is hereby corrected as shown below:

On the Title Page

Column 2, item (57), abstract, Line 3, delete "presence" and insert -- presence of --, therefor.

On page 2, Column 1, item (57), abstract, Line 5, delete "subjects" and insert -- subjecting --, therefor.

In the Specification

In Column 21, Line 50, delete "(a). —" and insert -- (a). --, therefor.

In Column 31, Line 49, delete "(purity about ≥ 99.5%," and insert -- (purity ≥ about 99.5%, --, therefor.

In Column 46, Line 11, delete "90 g/I" and insert -- 90 g/l --, therefor.

In Column 46, Line 50, delete "deioinized" and insert -- deionized --, therefor.

In Column 47, Line 47, delete "Prüfmaschine" and insert -- Prüfmaschinen --, therefor.

In Column 48, Line 43, delete "$a_{i,\ i=1,6}$" and insert -- $a_{i,\ i=1..6}$ --, therefor.

In the Claims

In Column 51, Line 64, Claim 11, delete "weight %" and insert -- weight-% --, therefor.

Signed and Sealed this
Thirty-first Day of December, 2019

Andrei Iancu
*Director of the United States Patent and Trademark Office*